(12) United States Patent
Birr et al.

(10) Patent No.: US 7,807,627 B2
(45) Date of Patent: Oct. 5, 2010

(54) BONE MORPHOGENETIC PROTEIN 4 AND OSTEOGENIC DEVICES AND PHARMACEUTICAL PRODUCTS CONTAINING THEREOF

(75) Inventors: Elli Birr, Kempele (FI); Mari Ulmanen, Tampere (FI); Oili Hietala, Oulu (FI); Marja Juustila, Liminka (FI); Heli Korkala, Oulu (FI); Pekka Jalovaara, Oulu (FI)

(73) Assignee: BBS-Bioactive Bone Substitutes Oy, Oulu (FI)

( * ) Notice: Subject to any disclaimer, the term of this patent is extended or adjusted under 35 U.S.C. 154(b) by 252 days.

(21) Appl. No.: 11/921,103

(22) PCT Filed: May 26, 2006

(86) PCT No.: PCT/FI2006/050213

§ 371 (c)(1),
(2), (4) Date: Jan. 12, 2008

(87) PCT Pub. No.: WO2006/125867

PCT Pub. Date: Nov. 30, 2006

(65) Prior Publication Data

US 2009/0214653 A1    Aug. 27, 2009

(30) Foreign Application Priority Data

May 27, 2005  (FI) ................................. 20055257
May 27, 2005  (FI) ................................. 20055258

(51) Int. Cl.
C12N 15/09   (2006.01)
C12N 15/11   (2006.01)
C12N 15/12   (2006.01)
C12N 15/63   (2006.01)
A61K 38/16   (2006.01)
A61K 38/17   (2006.01)
A61K 38/18   (2006.01)
C07K 14/435  (2006.01)
C07K 14/46   (2006.01)
C07K 14/47   (2006.01)
C07K 14/475  (2006.01)
C07K 14/51   (2006.01)

(52) U.S. Cl. ........................... 514/2; 530/350; 530/351; 530/300; 435/320.1; 435/325; 435/252.3; 435/254.11; 435/69.7; 536/23.1; 536/23.4; 536/23.5

(58) Field of Classification Search ....................... None
See application file for complete search history.

(56) References Cited

U.S. PATENT DOCUMENTS

| 5,266,683 A * | 11/1993 | Oppermann et al. ........ 530/326 |
| 6,083,690 A   | 7/2000  | Harris et al. |
| 6,245,889 B1  | 6/2001  | Wang et al. |
| 6,677,432 B1* | 1/2004  | Oppermann et al. ........ 530/350 |

OTHER PUBLICATIONS

Groeneveld et al. (2000, Eur. J. Endocrinology 142:9-21).*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Extended European Search Report dated Feb. 27, 2009.
Jian Q. Feng et al., "Deer antler tissue contains two types of bone morphogenetic protein 4 mRNA transcripts", Biochemica et Biophysica Acta, 1995, pp. 163-168, vol. 1263, No. 2, Elsevier Science B.V.
Database UNIPROT [Online} Feb. 15, 2005 "Bone Morphogenetic Protein 4" (Fragment, Bros Taurus) Retrieved From INIPROT/EBI Database Accession No. Q51419, See Amino Acids 274-389.
Database UNIPROT[Online] Nov. 1, 1997 "Bone Morphogenetic Protein 4 Precursor" (Dama Dama) Retrieved From UNIPROT/EBI, Database Accession No. Q29607, See Amino Acids 293-408.

* cited by examiner

*Primary Examiner*—Elizabeth C. Kemmerer
(74) *Attorney, Agent, or Firm*—Young & Thompson

(57) ABSTRACT

The present invention relates to reindeer bone formation inducing protein called bone morphogenetic protein 4 (BMP-4) and nucleotide molecules encoding the proteins and host cells expressing the proteins. The present invention relates also to the use of the BMP-4 for treating disorders related to bone and cartilage formation. Osteogenic devices and pharmaceutical compositions containing the proteins are also disclosed.

20 Claims, 8 Drawing Sheets

| 1 | atg<br>M | gat<br>D | ccg<br>P | agc<br>S | ccc<br>P | aag<br>K | cat<br>H | cac<br>H | cca<br>P | cag<br>Q | agg<br>R | gcc<br>A | cgg<br>R | 39 |
|---|---|---|---|---|---|---|---|---|---|---|---|---|---|---|
| | | | | | 5 | | | | | 10 | | | | |
| 40 | aag<br>K | aag<br>K | aat<br>N | aag<br>K | aac<br>N | tgc<br>C | cgg<br>R | cgc<br>R | cac<br>H | tcg<br>S | ccc<br>P | tat<br>Y | gtg<br>V | 78 |
| | | | 15 | | | | 20 | | | | | 25 | | |
| 79 | gac<br>D | ttc<br>F | agt<br>S | gat<br>D | gtg<br>V | ggc<br>G | tgg<br>W | aac<br>N | gac<br>D | tgg<br>W | att<br>I | gtg<br>V | gcc<br>A | 117 |
| | | | | | 30 | | | | 35 | | | | | |
| 118 | cca<br>P | cca<br>P | ggc<br>G | tac<br>Y | cag<br>Q | gcc<br>A | ttc<br>F | tac<br>Y | tgc<br>C | cac<br>H | ggg<br>G | gac<br>D | tgc<br>C | 156 |
| | | 40 | | | | 45 | | | | | 50 | | | |
| 157 | ccc<br>P | ttt<br>F | ccg<br>P | ctg<br>L | gcc<br>A | gac<br>D | cac<br>H | ctc<br>L | aac<br>N | tcc<br>S | acc<br>T | aac<br>N | cac<br>H | 195 |
| | | | 55 | | | | 60 | | | | | 65 | | |
| 196 | gcc<br>A | att<br>I | gtg<br>V | cag<br>Q | acc<br>T | ctc<br>L | gtc<br>V | aac<br>N | tct<br>S | gtc<br>V | aac<br>N | tcc<br>S | agc<br>S | 234 |
| | | | | | 70 | | | | | 75 | | | | |
| 235 | atc<br>I | ccc<br>P | aaa<br>K | gcc<br>A | tgt<br>C | tgt<br>C | gtt<br>V | ccc<br>P | acc<br>T | gaa<br>E | ctg<br>L | agc<br>S | gcc<br>A | 273 |
| | | | 80 | | | | 85 | | | | | 90 | | |
| 274 | atc<br>I | tcc<br>S | atg<br>M | ctg<br>L | tac<br>Y | ttg<br>L | gat<br>D | gag<br>E | tat<br>Y | gac<br>D | aaa<br>K | gtg<br>V | gtt<br>V | 312 |
| | | | | | 95 | | | | | 100 | | | | |
| 313 | ctg<br>L | aaa<br>K | aat<br>N | tat<br>Y | cag<br>Q | gag<br>E | atg<br>M | gta<br>V | gtg<br>V | gag<br>E | gga<br>G | tgt<br>C | ggg<br>G | 351 |
| | 105 | | | | | 110 | | | | | 115 | | | |
| 352 | tgc<br>C | cgc<br>R | aag<br>K | ctt<br>L | ggg<br>G | ccc<br>P | gaa<br>E | caa<br>Q | aaa<br>K | ctc<br>L | atc<br>I | tca<br>S | gaa<br>E | 390 |
| | | | 120 | | | | | 125 | | | | | 130 | |
| 391 | gag<br>E | gat<br>D | ctg<br>L | aat<br>N | agc<br>S | gcc<br>A | gtc<br>V | gac<br>D | cat<br>H | cat<br>H | cat<br>H | cat<br>H | cat<br>H | 429 |
| | | | | | 135 | | | | | 140 | | | | |
| 430 | cat<br>H | tga<br>- | | | | | | | | | | | | 436 |

Fig. 5

| | | | | | | | | | | | | | |
|---|---|---|---|---|---|---|---|---|---|---|---|---|---|
| 1 | atg M | aaa K | tac Y | ctg L | ctg L 5 | ccg P | acc T | gct A | gct A | gct A 10 | ggt G | ctg L | ctg L | 39 |
| 40 | ctc L | ctc L 15 | gct A | gcc A | cag Q | ccg P | gcg A 20 | atg M | gcc A | atg M | gat D | atc I 25 | gga G | 78 |
| 79 | att I | aat N | tcg S | gat D 30 | ccg P | agc S | ccc P | aag K | cat H 35 | cac H | cca P | cag Q | agg R | 117 |
| 118 | gcc A 40 | cgg R | aag K | aag K | aat N | aag K 45 | aac N | tgc C | cgg R | cgc R | cac H 50 | tcg S | ccc P | 156 |
| 157 | tat Y | gtg V | gac D 55 | ttc F | agt S | gat D | gtg V | ggc G 60 | tgg W | aac N | gac D | tgg W | att I 65 | 195 |
| 196 | gtg V | gcc A | cca P | cca P | ggc G 70 | tac Y | cag Q | gcc A | ttc F | tac Y 75 | tgc C | cac H | ggg G | 234 |
| 235 | gac D | tgc C 80 | ccc P | ttt F | ccg P | ctg L | gcc A 85 | gac D | cac H | ctc L | aac N | tcc S 90 | acc T | 273 |
| 274 | aac N | cac H | gcc A | att I 95 | gtg V | cag Q | acc T | ctc L | gtc V 100 | aac N | tct S | gtc V | aac N | 312 |
| 313 | tcc S 105 | agc S | atc I | ccc P | aaa K | gcc A 110 | tgt C | tgt C | gtt V | ccc P 115 | acc T | gaa E | ctg L | 351 |
| 352 | agc S | gcc A | atc I 120 | tcc S | atg M | ctg L | tac Y 125 | ttg L | gat D | gag E | tat Y | gac D 130 | aaa K | 390 |
| 391 | gtg V | gtt V | ctg L | aaa K 135 | aat N | tat Y | cag Q | gag E | atg M 140 | gta V | gtg V | gag E | gga G | 429 |
| 430 | tgt C | ggg G 145 | tgc C | cgc R | aag K | ctt L | gcg A 150 | gcc A | gca A | ctc L | gag E | cac H 155 | cac H | 468 |
| 469 | cac H | cac H | cac H | cac H 160 | tga | | | | | | | | | |

Fig. 6

| | | | | | | | | | | | | |
|---|---|---|---|---|---|---|---|---|---|---|---|---|
| 1 | atg<br>M | tct<br>S | ggt<br>G | tct<br>S | cat<br>H<br>5 | cat<br>H | cat<br>H | cat<br>H | cat<br>H | cat<br>H<br>10 | agc<br>S | agc<br>S | 39 |
| 40 | ggc<br>G | atc<br>I | gaa<br>E<br>15 | ggc<br>G | cgc<br>R | ggt<br>G | agc<br>S | ccc<br>P<br>20 | aag<br>K | cat<br>H | cac<br>H | cca<br>P | 78 |
| 79 | cag<br>Q | agg<br>R<br>25 | gcc<br>A | cgg<br>R | aag<br>K | aag<br>K<br>30 | aat<br>N | aag<br>K | aac<br>N | tgc<br>C | cgg<br>R<br>35 | cgc<br>R | 117 |
| 118 | cac<br>H | tcg<br>S | ccc<br>P | tat<br>Y<br>40 | gtg<br>V | gac<br>D | ttc<br>F | agt<br>S | gat<br>D<br>45 | gtg<br>V | ggc<br>G | tgg<br>W | 156 |
| 157 | aac<br>N | gac<br>D<br>50 | tgg<br>W | att<br>I | gtg<br>V | gcc<br>A | cca<br>P<br>55 | cca<br>P | ggc<br>G | tac<br>Y | cag<br>Q | gcc<br>A<br>60 | 195 |
| 196 | ttc<br>F | tac<br>Y | tgc<br>C | cac<br>H | ggg<br>G<br>65 | gac<br>D | tgc<br>C | ccc<br>P | ttt<br>F | ccg<br>P<br>70 | ctg<br>L | gcc<br>A | 234 |
| 235 | gac<br>D | cac<br>H | ctc<br>L<br>75 | aac<br>N | tcc<br>S | acc<br>T | aac<br>N | cac<br>H<br>80 | gcc<br>A | att<br>I | gtg<br>V | cag<br>Q | 273 |
| 274 | acc<br>T<br>85 | ctc<br>L | gtc<br>V | aac<br>N | tct<br>S | gtc<br>V<br>90 | aac<br>N | tcc<br>S | agc<br>S | atc<br>I | ccc<br>P<br>95 | aaa<br>K | 312 |
| 313 | gcc<br>A | tgt<br>C | tgt<br>C | gtt<br>V<br>100 | ccc<br>P | acc<br>T | gaa<br>E | ctg<br>L | agc<br>S<br>105 | gcc<br>A | atc<br>I | tcc<br>S | 351 |
| 352 | atg<br>M | ctg<br>L<br>110 | tac<br>Y | ttg<br>L | gat<br>D | gag<br>E | tat<br>Y<br>115 | gac<br>D | aaa<br>K | gtg<br>V | gtt<br>V | ctg<br>L<br>120 | 390 |
| 391 | aaa<br>K | aat<br>N | tat<br>Y | cag<br>Q | gag<br>E<br>125 | atg<br>M | gta<br>V | gtg<br>V | gag<br>E | gga<br>G<br>130 | tgt<br>C | ggg<br>G | 429 |
| 430 | tgc<br>C | cgc<br>R<br>135 | tag<br>stop | gat<br>D | ccg<br>P | taa<br>stop<br>140 | | | | | | | 468 |

Fig. 7

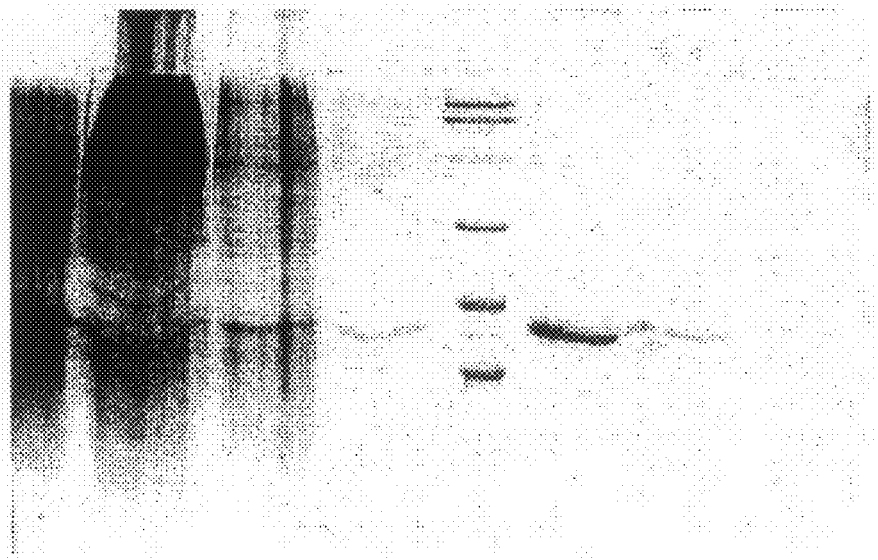
Fig. 8
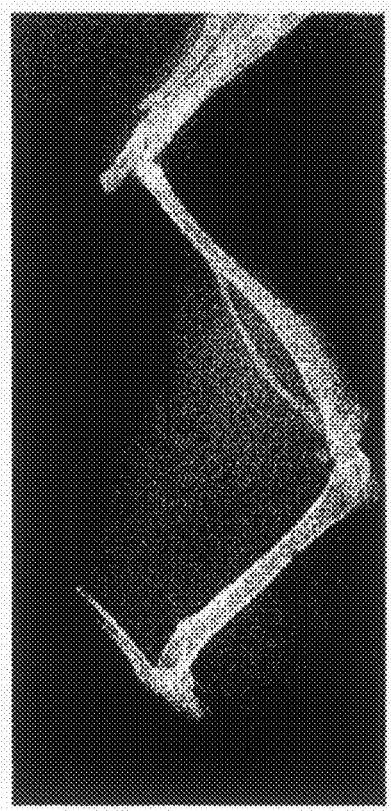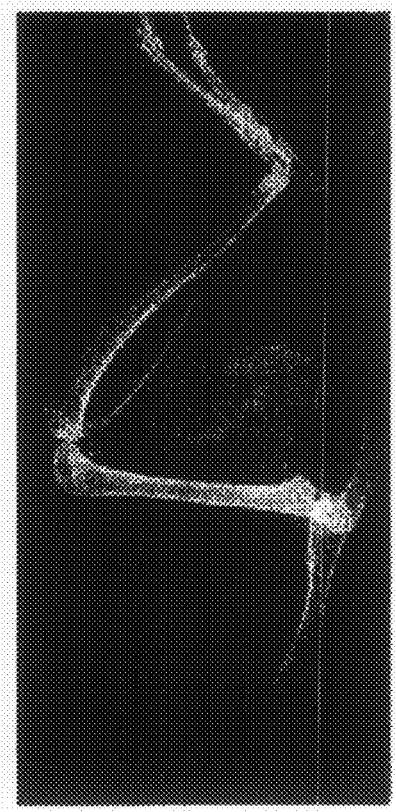
Fig. 9

SEQUENCE LISTING

<160> NUMBER OF SEQ ID NOS: 38

<210> SEQ ID NO 1
<211> LENGTH: 116
<212> TYPE: PRT
<213> ORGANISM: Rangifer tarandus tarandus

<400> SEQUENCE: 1

```
Ser Pro Lys His His Pro Gln Arg Ala Arg Lys Lys Asn Lys Asn Cys
1               5                   10                  15

Arg Arg His Ser Pro Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115
```

<210> SEQ ID NO 2
<211> LENGTH: 116
<212> TYPE: PRT
<213> ORGANISM: Homo sapiens sapiens

<400> SEQUENCE: 2

```
Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45
```

```
Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                 85                  90                  95

Tyr Asp Lys Val Val Leu Lys Asn Tyr Gln Glu Met Val Glu Gly
                100                 105                 110

Cys Gly Cys Arg
        115

<210> SEQ ID NO 3
<211> LENGTH: 116
<212> TYPE: PRT
<213> ORGANISM: Oryctolagus sp.

<400> SEQUENCE: 3

Ser Leu Lys His His Pro Gln Arg Ala Arg Lys Lys Asn Lys Asn Cys
 1               5                  10                  15

Arg Arg His Ala Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
                35                  40                  45

Cys Pro Phe Pro Leu Ala Asp His Phe Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                 85                  90                  95

Tyr Asp Lys Val Val Leu Lys Asn Tyr Gln Glu Met Val Glu Gly
                100                 105                 110

Cys Gly Cys Arg
        115

<210> SEQ ID NO 4
<211> LENGTH: 116
<212> TYPE: PRT
<213> ORGANISM: Bos taurus

<400> SEQUENCE: 4

Ser Pro Lys His His Pro Gln Arg Ala Arg Lys Lys Asn Lys Asn Cys
 1               5                  10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
                35                  40                  45

Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                 85                  90                  95

Tyr Asp Lys Val Val Leu Lys Asn Tyr Gln Glu Met Val Glu Gly
                100                 105                 110

Cys Gly Cys Arg
        115
```

-continued

```
<210> SEQ ID NO 5
<211> LENGTH: 116
<212> TYPE: PRT
<213> ORGANISM: Canis sp.

<400> SEQUENCE: 5

Ser Pro Lys His His Ala Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 6
<211> LENGTH: 116
<212> TYPE: PRT
<213> ORGANISM: Cervus dama

<400> SEQUENCE: 6

Ser Pro Lys His His Pro Gln Arg Ala Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45

Cys Pro Phe Pro Leu Ala Asp His Leu Asn Ser Thr Asn His Ala Ile
    50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 7
<211> LENGTH: 116
<212> TYPE: PRT
<213> ORGANISM: Rattus sp.

<400> SEQUENCE: 7

Ser Pro Lys His His Pro Gln Arg Ser Arg Lys Lys Asn Lys Asn Cys
1               5                   10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
        35                  40                  45
```

```
Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 8
<211> LENGTH: 116
<212> TYPE: PRT
<213> ORGANISM: Mus musculus

<400> SEQUENCE: 8

Ser Pro Lys His His Pro Gln Arg Ser Arg Lys Asn Lys Asn Cys
 1               5                  10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
            35                  40                  45

Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115

<210> SEQ ID NO 9
<211> LENGTH: 116
<212> TYPE: PRT
<213> ORGANISM: Suncus murinus

<400> SEQUENCE: 9

Ser Pro Lys His His Pro Gln Arg Ala Arg Lys Lys Asn Lys Asn Cys
 1               5                  10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
            35                  40                  45

Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
            100                 105                 110

Cys Gly Cys Arg
        115
```

```
<210> SEQ ID NO 10
<211> LENGTH: 114
<212> TYPE: PRT
<213> ORGANISM: Gallus gallus

<400> SEQUENCE: 10

Ser Pro Lys His His Gly Ser Arg Lys Asn Lys Asn Cys Arg Arg
1               5                   10                  15

His Ala Leu Tyr Val Asp Phe Ser Asp Val Gly Trp Asn Asp Trp Ile
            20                  25                  30

Val Ala Pro Pro Gly Tyr Gln Ala Phe Tyr Cys His Gly Asp Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Ser Ile Pro Lys Ala Cys Cys Val
65                  70                  75                  80

Pro Thr Glu Leu Ser Ala Ile Ser Met Leu Tyr Leu Asp Glu Tyr Asp
                85                  90                  95

Lys Val Val Leu Lys Asn Tyr Gln Glu Met Val Val Glu Gly Cys Gly
            100                 105                 110

Cys Arg

<210> SEQ ID NO 11
<211> LENGTH: 114
<212> TYPE: PRT
<213> ORGANISM: Xenopus laevis

<400> SEQUENCE: 11

Ser Pro Lys Gln Gln Arg Pro Arg Lys Lys Asn Lys His Cys Arg Arg
1               5                   10                  15

His Ser Leu Tyr Val Asp Phe Ser Asp Val Gly Trp Asn Asp Trp Ile
            20                  25                  30

Val Ala Pro Pro Gly Tyr Gln Ala Phe Tyr Cys His Gly Asp Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Ser Ile Pro Lys Ala Cys Cys Val
65                  70                  75                  80

Pro Thr Glu Leu Ser Ala Ile Ser Met Leu Tyr Leu Asp Glu Tyr Asp
                85                  90                  95

Lys Val Val Leu Lys Asn Tyr Gln Glu Met Val Val Glu Gly Cys Gly
            100                 105                 110

Cys Arg

<210> SEQ ID NO 12
<211> LENGTH: 113
<212> TYPE: PRT
<213> ORGANISM: Danio rerio

<400> SEQUENCE: 12

Ser Pro Lys Gln Arg Gly Arg Lys Arg Asn Arg Asn Cys Arg Arg His
1               5                   10                  15

Ala Leu Tyr Val Asp Phe Ser Asp Val Gly Trp Asn Asp Trp Ile Val
            20                  25                  30

Ala Pro Pro Gly Tyr Gln Ala Tyr Tyr Cys His Gly Glu Cys Pro Phe
        35                  40                  45

Pro Leu Ala Asp His Leu Asn Ser Thr Asn His Ala Ile Val Gln Thr
    50                  55                  60
```

```
Leu Val Asn Ser Val Asn Thr Asn Ile Pro Lys Ala Cys Cys Val Pro
 65                  70                  75                  80

Thr Glu Leu Ser Ala Ile Ser Met Leu Tyr Leu Asp Glu Thr Asp Arg
                 85                  90                  95

Val Val Leu Lys Asn Tyr Gln Glu Met Val Val Glu Gly Cys Gly Cys
            100                 105                 110

Arg

<210> SEQ ID NO 13
<211> LENGTH: 114
<212> TYPE: PRT
<213> ORGANISM: Homo sapiens

<400> SEQUENCE: 13

Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg

<210> SEQ ID NO 14
<211> LENGTH: 114
<212> TYPE: PRT
<213> ORGANISM: Cervus dama

<400> SEQUENCE: 14

Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg

<210> SEQ ID NO 15
<211> LENGTH: 114
<212> TYPE: PRT
<213> ORGANISM: Mus musculus
```

-continued

```
<400> SEQUENCE: 15

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 16
<211> LENGTH: 114
<212> TYPE: PRT
<213> ORGANISM: Xenopus laevis

<400> SEQUENCE: 16

Gln Ala Arg His Lys Gln Arg Lys Arg Leu Lys Ser Ser Cys Arg Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Thr Asn Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Ala Lys His Lys Gln Arg Lys Arg Gly Thr
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic peptide

<400> SEQUENCE: 18

Gln Ala Lys His Lys Gln Arg Lys Arg Gly Thr
```

<210> SEQ ID NO 19
<211> LENGTH: 31
<212> TYPE: DNA
<213> ORGANISM: Artificial sequence
<220> FEATURE:
<223> OTHER INFORMATION: Synthetic nucleotide

<400> SEQUENCE: 19
ggatccgagc cccaagcatc acccacagag g                          31

<210> SEQ ID NO 20
<211> LENGTH: 30
<212> TYPE: DNA
<213> ORGANISM: Artificial sequence
<220> FEATURE:
<223> OTHER INFORMATION: Synthetic nucleotide

<400> SEQUENCE: 20
catcacctcc ctacacccac ggcgttcgaa                            30

<210> SEQ ID NO 21
<211> LENGTH: 31
<212> TYPE: DNA
<213> ORGANISM: Artificial sequence
<220> FEATURE:
<223> OTHER INFORMATION: Synthetic nucleotide

<400> SEQUENCE: 21
ccgcggtagc cccaagcatc acccacagag g                          31

<210> SEQ ID NO 22
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 22
catcacctcc ctacacccac ggcgatccta gg                         32

<210> SEQ ID NO 23
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 23
taatacgact cactataggg cga                                   23

<210> SEQ ID NO 24
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 24
cataagatat cacagtggat tta                                   23

<210> SEQ ID NO 25
<211> LENGTH: 22
<212> TYPE: DNA
<213> ORGANISM: Artificial sequence
<220> FEATURE:

```
<223> OTHER INFORMATION: Synthetic nucleotide

<400> SEQUENCE: 25
agaggtatat attaatgtat cg                                              22

<210> SEQ ID NO 26
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 26
gacttatcgc ggcagctggt a                                               21

<210> SEQ ID NO 27
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 27
taatacgact cactataggg cga                                             23

<210> SEQ ID NO 28
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 28
ggcgactcgt tattgatcg                                                  19

<210> SEQ ID NO 29
<211> LENGTH: 44
<212> TYPE: DNA
<213> ORGANISM: Artificial sequence
<220> FEATURE:
<223> OTHER INFORMATION: Synthetic nucleotide

<400> SEQUENCE: 29
cgggatccgc aagcaaaaca taaacagcgc aaacgcggta cccc                      44

<210> SEQ ID NO 30
<211> LENGTH: 44
<212> TYPE: DNA
<213> ORGANISM: Artificial sequence
<220> FEATURE:
<223> OTHER INFORMATION: Synthetic nucleotide

<400> SEQUENCE: 30
gccctaggcg ttcgttttgt atttgtcgcc tttgcgccat gggg                      44

<210> SEQ ID NO 31
<211> LENGTH: 29
<212> TYPE: DNA
<213> ORGANISM: Artificial sequence
<220> FEATURE:
<223> OTHER INFORMATION: Synthetic nucleotide

<400> SEQUENCE: 31
caggtaccag ccccaagcat cacccacag                                       29

<210> SEQ ID NO 32
```

```
<211> LENGTH: 27
<212> TYPE: DNA
<213> ORGANISM: Artificial sequence
<220> FEATURE:
<223> OTHER INFORMATION: Synthetic nucleotide

<400> SEQUENCE: 32
cacctcccta cacccacggc gttcgaa                                              27

<210> SEQ ID NO 33
<211> LENGTH: 144
<212> TYPE: PRT
<213> ORGANISM: Rangifer tarandus tarandus

<400> SEQUENCE: 33

Met Asp Pro Ser Pro Lys His His Pro Gln Arg Ala Arg Lys Lys Asn
1               5                   10                  15

Lys Asn Cys Arg Arg His Ser Pro Tyr Val Asp Phe Ser Asp Val Gly
            20                  25                  30

Trp Asn Asp Trp Ile Val Ala Pro Pro Gly Tyr Gln Ala Phe Tyr Cys
        35                  40                  45

His Gly Asp Cys Pro Phe Pro Leu Ala Asp His Leu Asn Ser Thr Asn
    50                  55                  60

His Ala Ile Val Gln Thr Leu Val Asn Ser Val Asn Ser Ser Ile Pro
65                  70                  75                  80

Lys Ala Cys Cys Val Pro Thr Glu Leu Ser Ala Ile Ser Met Leu Tyr
                85                  90                  95

Leu Asp Glu Tyr Asp Lys Val Val Leu Lys Asn Tyr Gln Glu Met Val
            100                 105                 110

Val Glu Gly Cys Gly Cys Arg Lys Leu Gly Pro Glu Gln Lys Leu Ile
        115                 120                 125

Ser Glu Glu Asp Leu Asn Ser Ala Val Asp His His His His His
    130                 135                 140

<210> SEQ ID NO 34
<211> LENGTH: 435
<212> TYPE: DNA
<213> ORGANISM: Rangifer tarandus tarandus

<400> SEQUENCE: 34
atggatccga gccccaagca tcacccacag agggcccgga agaagaataa gaactgccgg        60
cgccactcgc cctatgtgga cttcagtgat gtgggctgga acgactggat tgtggcccca       120
ccaggctacc aggccttcta ctgccacggg gactgcccct ttccgctggc cgaccacctc       180
aactccacca ccacgccat tgtgcagacc ctcgtcaact ctgtcaactc cagcatcccc        240
aaagcctgtt gtgttcccac cgaactgagc gccatctcca tgctgtactt ggatgagtat       300
gacaaagtgg ttctgaaaaa ttatcaggag atggtagtgg agggatgtgg gtgccgcaag       360
cttgggcccg aacaaaaact catctcagaa gaggatctga tagcgccgt cgaccatcat        420 catcatcatc attga                                                        435

<210> SEQ ID NO 35
<211> LENGTH: 160
<212> TYPE: PRT
<213> ORGANISM: Rangifer tarandus tarandus

<400> SEQUENCE: 35

Met Lys Tyr Leu Leu Pro Thr Ala Ala Ala Gly Leu Leu Leu Leu Ala
1               5                   10                  15
```

```
Ala Gln Pro Ala Met Ala Met Asp Ile Gly Ile Asn Ser Asp Pro Ser
            20                  25                  30

Pro Lys His His Pro Gln Arg Ala Arg Lys Lys Asn Lys Asn Cys Arg
         35                  40                  45

Arg His Ser Pro Tyr Val Asp Phe Ser Asp Val Gly Trp Asn Asp Trp
     50                  55                  60

Ile Val Ala Pro Pro Gly Tyr Gln Ala Phe Tyr Cys His Gly Asp Cys
65                  70                  75                  80

Pro Phe Pro Leu Ala Asp His Leu Asn Ser Thr Asn His Ala Ile Val
             85                  90                  95

Gln Thr Leu Val Asn Ser Val Asn Ser Ser Ile Pro Lys Ala Cys Cys
            100                 105                 110

Val Pro Thr Glu Leu Ser Ala Ile Ser Met Leu Tyr Leu Asp Glu Tyr
            115                 120                 125

Asp Lys Val Val Leu Lys Asn Tyr Gln Glu Met Val Val Glu Gly Cys
            130                 135                 140

Gly Cys Arg Lys Leu Ala Ala Ala Leu Glu His His His His His His
145                 150                 155                 160

<210> SEQ ID NO 36
<211> LENGTH: 483
<212> TYPE: DNA
<213> ORGANISM: Rangifer tarandus tarandus

<400> SEQUENCE: 36
atgaaatacc tgctgccgac cgctgctgct ggtctgctgc tcctcgctgc ccagccggcg     60
atggccatgg atatcggaat taattcggat ccgagcccca agcatcaccc acagagggcc    120
cggaagaaga ataagaactg ccggcgccac tcgccctatg tggacttcag tgatgtgggc    180
tggaacgact ggattgtggc cccaccaggc taccaggcct tctactgcca cggggactgc    240 cccttccgc tggccgacca cctcaactcc accaaccacg ccattgtgca gaccctcgtc      300
aactctgtca actccagcat ccccaaagcc tgttgtgttc ccaccgaact gagcgccatc    360
tccatgctgt acttggatga gtatgacaaa gtggttctga aaaattatca ggagatggta    420
gtggagggat gtgggtgccg caagcttgcg gccgcactcg agcaccacca ccaccaccac    480
tga                                                                  483

<210> SEQ ID NO 37
<211> LENGTH: 134
<212> TYPE: PRT
<213> ORGANISM: Rangifer tarandus tarandus

<400> SEQUENCE: 37

Met Ser Gly Ser His His His His His His Ser Gly Ile Glu Gly
1               5                   10                  15

Arg Gly Ser Pro Lys His His Pro Gln Arg Ala Arg Lys Lys Asn Lys
             20                  25                  30

Asn Cys Arg Arg His Ser Pro Tyr Val Asp Phe Ser Asp Val Gly Trp
         35                  40                  45

Asn Asp Trp Ile Val Ala Pro Pro Gly Tyr Gln Ala Phe Tyr Cys His
     50                  55                  60

Gly Asp Cys Pro Phe Pro Leu Ala Asp His Leu Asn Ser Thr Asn His
65                  70                  75                  80

Ala Ile Val Gln Thr Leu Val Asn Ser Val Asn Ser Ser Ile Pro Lys
             85                  90                  95

Ala Cys Cys Val Pro Thr Glu Leu Ser Ala Ile Ser Met Leu Tyr Leu
```

```
                        100                 105                 110
Asp Glu Tyr Asp Lys Val Val Leu Lys Asn Tyr Gln Glu Met Val Val
            115                 120                 125

Glu Gly Cys Gly Cys Arg
        130

<210> SEQ ID NO 38
<211> LENGTH: 414
<212> TYPE: DNA
<213> ORGANISM: Rangifer tarandus tarandus

<400> SEQUENCE: 38
atgtctggtt ctcatcatca tcatcatcat agcagcggca tcgaaggccg cggtagcccc      60
aagcatcacc cacagagggc ccggaagaag aataagaact gccggcgcca ctcgccctat     120
gtggacttca gtgatgtggg ctggaacgac tggattgtgg ccccaccagg ctaccaggcc     180
ttctactgcc acggggactg ccccttccg ctggccgacc acctcaactc caccaaccac      240
gccattgtgc agaccctcgt caactctgtc aactccagca tccccaaagc ctgttgtgtt     300
cccaccgaac tgagcgccat ctccatgctg tacttggatg agtatgacaa agtggttctg     360
aaaaattatc aggagatggt agtggaggga tgtgggtgcc gctaggatcc gtaa           414
```

BONE MORPHOGENETIC PROTEIN 4 AND OSTEOGENIC DEVICES AND PHARMACEUTICAL PRODUCTS CONTAINING THEREOF

This is a 371 National Stage application of International application no. PCT/FI2006/050213, filed May 26, 2006, which claims priority to Finnish application nos. 20055257 and 20055258, filed May 27, 2005. The entire contents of the above-referenced applications are hereby incorporated by reference in their entirety.

FIELD OF THE INVENTION

The present invention relates to bone formation inducing proteins called bone morphogenetic proteins (BMP), especially BMP-4, nucleic acid molecules encoding said proteins, vectors containing said nucleic acid molecules and host cells expressing said proteins. The present invention relates also to the use of said bone morphogenetic proteins for treating disorders, such as disorders related to bone and cartilage formation. The present invention further relates to osteogenic devices and pharmaceutical compositions containing said proteins.

BACKGROUND OF THE INVENTION

The phenomenon of osteoinduction was recognized by Lancroix in 1945 when he demonstrated that acid alcohol bone extracts induced heterotopic bone formation in ectopic sites. Twenty years later Urist and his co-workers decalcified bone matrix and observed new cartilage and bone formation when implanted intramuscularly. These discoveries led to isolation and purification of bone inducing agent named BMPs from bone matrix of different species and years later to cloning and characterization of several cDNAs encoding these novel proteins. The biological activity of BMPs has been determined by bioassay in rat or mouse muscle bounces or by ALP measurements in mammalian cell cultures.

Previous studies since 1965 have shown that BMPs are part of the TGF-β superfamily and like all the family members they have multiple effects on cell migration, growth and differentiation especially in bone formation and tissue repair but also in embryogenesis or cancer. They are low molecular weight hydrophobic glycoproteins which are soluble to chaotrophic agents such as urea and guanidinium hydrochloride but are resistant to several proteases, for example collagenases.

BMPs are produced as large precursor molecules which are processed proteolytically to mature peptides after the translation. Like all the members of TGF-β superfamily, BMPs have the pattern of seven cysteine residues in their C-terminal mature region. Between these cysteines there are three disulfide bonds within mature BMP monomers and one disulfide bond which combines two monomers into a biologically active BMP dimer.

BMPs act through specific transmembrane receptors located on cell surface of the target cells. The BMP receptors are serin-threonin kinases which resemble TGF-β receptors and are divided into two subgroups: type I and type II receptors. BMPs can bind strongly only to the heterotetrameric complex of these receptors. This complex formation is essential to the BMP signal transduction. Inside the target cell, BMP signals are transmitted to the nucleus via specific signal molecules called Smads, which are also responsible for suppression of BMP signals.

Until now, 16 different BMPs have been characterized and seven of them (BMPs 2-7 and 9) have shown to be able to induce bone formation when implanted in ectopic sites. According to the amino acid sequence of the mature part these BMPs are divided into two subgroups. BMPs 2 and 4 are 86% identical and BMPs 5, 6 and 7 are 78% identical. Between these two groups the identity is only about 56%. The amino acid sequence of BMP-3 is about 45% alike with BMPs 2 and 4 and BMP-9 is 50-55% identical with BMPs 2, 4, 5, 6 and 7. Due to high homology and small variety in size, BMPs are quite difficult, very time consuming and expensive to separate, purify and identify from each other at protein level. This is the reason why most of the BMPs are nowadays being produced using molecular biological tools. Different kinds of recombinant protein techniques have been tested and both eukaryotic and prokaryotic systems have been utilized.

Majority of research has focused on human recombinant BMPs, but with regard to effective bone induction antlers of Cervidae family form an interesting research area. Antlers are bony cranial organs typical to the Cervidae family and they differ from Bovidae horns in their growing pattern. Antlers grow from the tip and males cast them away once per year. It has been suggested that antlers are the fastest growing structures through the mammalian species and they are known to be the only structures that regenerate completely every year. Antlers are formed by modified endochondral ossification meaning that the process is performed through the highly vascularized cartilage model which is calcified and finally transformed into bone. Antlers form an interesting model of adult regenerating mineralized tissue and bone remodeling has been shown to continue until the time of antler casting. Although the ultimate reason for the amazing speed of antler growth has not yet been resolved, antlers have been shown to contain several BMPs. Deer antler has been proven to express BMP-2 and BMP-4 (Feng et al. 1997 Biochim Biophys Acta 1350:47-52; Feng et al. 1995 Biochim Biophys Acta 1263: 163-168). In addition reindeer antlers express BMP-3b (Kapanen et al. 2002 J Biomed Mat Res 59:78-83). Yet, it is also possible that there is one or more totally uncovered factor(s) which are responsible for antler growth speed.

Due to their osteoinductive capacity, both BMPs extracted from demineralized bone matrix and BMPs produced by recombinant technique are very interesting and highly potential alternatives to bone grafting. Different BMPs have been used in many experimental and clinical studies.

Bone morphogenetic protein 4 has been isolated from different origins including some mammalian species like human, mouse, rat, rabbit and dog. Like BMP-2 it has also been isolated from antler of Texas fallow deer a member of Cervidae family (Feng et al. 1997; Feng et al. 1995). However, the functionality and effect of deer BMP-4 has not been demonstrated as it has not been produced in any expression systems.

Until now, BMP-3b has been the only BMP characterized in reindeer antler tissue (Kapanen et al. 2002).

Several in vitro studies have shown that BMP-4 signaling is required for chondrogenesis to convert chondrogenic precursor cells into chondrocytes. Its expression is enhanced by the impact of fracture and like BMP-3, -7 and -8 it shows a restricted period of expression from day 14 to 21. It is expressed in callus-forming tissue before callus formation. It also acts as a chemoattractive protein for primary human mesenchymal progenitor cells. Furthermore, BMP-4 has been shown to play a critical role in induction of bone formation both in vivo and in vitro and like BMP-2 its influence on embryogenesis can not be replaced by any other BMP. Though, functions and activity of BMP-4 have been under constant study for over the decade and though human BMP-4 has been produced as recombinant protein, until now, nobody has published information of the biological activity of BMP-4 cloned from the antler tissue of any member of Cervidae family.

U.S. Pat. No. 6,245,889 discloses purified human BMP-2 and BMP-4 proteins and processes for producing them. Also a pharmaceutical composition comprising said BMP-4 is disclosed. As generally known in the art, these proteins and compositions may be used in the treatment of bone and cartilage defects and in wound healing and related tissue repair. Further, said pharmaceutical composition may include a matrix capable of delivering said BMP proteins to the site of bone and/or cartilage damage, providing a structure for the developing bone and cartilage and optimally capable of being resorbed into the body. Such matrices may be formed of materials presently in use for other implanted medical applications.

U.S. Pat. No. 5,399,677 discloses DNA molecules encoding mutant forms of bone morphogenetic proteins. The mutant forms of BMP can be produced bacterially and refolded to produce biologically active homodimers or heterodimers of BMP. A method of making such mutant BMP is also disclosed. Said mutant forms are useful since they are correctly folded when produced in bacterial hosts.

WO 98/51354 discloses osteogenic devices and methods of use thereof for repair of bone and cartilage defects. The method for producing new bone growth at bone defect site in a mammal comprises the step of implanting in a defect site a calcium phosphate matrix comprising at least one osteogenic protein. Said osteogenic proteins include several morphogens, such as bone morphogenetic proteins.

EP 1131087 discloses further use for morphogenetic proteins, such as BMP proteins. It is shown that exposing cancer cells to morphogens inhibits cancer cell growth and causes such cells to differentiate away from the cancerous phenotype. The use of morphogen can influence cancer cell fate and, in turn, alleviate the symptoms of cancer. Preferred morphogens disclosed include BMP-4.

Although some applications of known BMP proteins as bone and cartilage forming inducers or for alleviating the symptoms of cancer are already known, there is still need for better methods for isolating such proteins and for better morphogenetic proteins, for example ones which possess more efficient bone forming properties or are more soluble. Such proteins would be useful for better therapeutic methods and applications. Also methods for producing such proteins would be useful.

SUMMARY OF THE INVENTION

Surprisingly in the present invention new BMP-4 protein isolated from reindeer, despite having high sequence homology with already known bone morphogenetic proteins, has very advantageous properties related to bone and cartilage forming. Said properties are substantially better than the properties of the known corresponding bone morphogenetic proteins. Said bone morphogenetic protein of the present invention and homologues thereof are useful for inducing bone and cartilage formation in several kinds of applications, such as therapeutic applications.

One aspect of the present invention relates to an isolated bone morphogenetic protein or homologue, analog, derivative or fragment thereof containing the essential amino acids of amino acid sequence of SEQ ID NO: 1.

Another aspect of the present invention relates to a heparin binding site combined with said bone morphogenetic protein. The heparin binding site improves the expression of the recombinant BMP protein and also improves the biological activity thereof.

Another aspect of the present invention relates to an isolated DNA molecule encoding said bone morphogenetic protein.

Still another aspect of the present invention relates to a nucleic acid vector containing said isolated DNA molecule.

Still another aspect of the present invention relates to a recombinant host cell containing said DNA molecule or the nucleic acid vector mentioned above.

Still another aspect of the present invention relates to bone morphogenetic protein which is produced by culturing said recombinant host cell to express said bone morphogenetic protein and by recovering said bone morphogenetic protein from said host cell.

Still another aspect of the present invention relates to a recombinant host cell expressing said bone morphogenetic protein.

Still another aspect of the present invention relates to a pharmaceutical composition containing said bone morphogenetic protein.

Still another aspect of the present invention relates to said isolated bone morphogenetic protein for use as medicament.

Still another aspect of the present invention relates to the use of said isolated bone morphogenetic protein for manufacturing medicament for disorders related to bone or cartilage defects wherein regeneration, repair or growth thereof is desired, or other diseases, such as cancer.

Still another aspect of the present invention relates to an osteogenic device for treating said disorders said device containing said isolated bone morphogenetic protein.

Still another aspect of the present invention relates to a method for inducing the formation of cartilage and/or bone by treating said cartilage and/or bone with said isolated bone morphogenetic protein.

Still another aspect of the present invention relates to a method for treating said disorders related to bone or cartilage defects wherein regeneration, repair or growth thereof is desired, or other diseases, such as cancer, by administering said isolated bone morphogenetic protein to a patient suffering from said disorders.

Still another aspect of the present invention relates to a method for improving the expression of a recombinant BMP protein in a bacterial host by adding a heparin binding site to the amino terminus of said protein to be expressed.

Still another aspect of the present invention relates to a method for improving or enhancing the biological activity of a recombinant BMP protein by adding a heparin binding site to the amino terminus of said protein.

Still another aspect of the present invention relates to a method for expressing a BMP protein in a bacterial host, such as *E. Coli*, by adding a heparin binding site to the amino terminus of said protein wherein the protein shows lowered immunogenicity when compared to a BMP expressed in for example yeast host.

BRIEF DESCRIPTION OF THE DRAWINGS

FIG. 5 shows amino acid (SEQ ID NO: 33) and nucleotide (SEQ ID NO: 34) sequences of reindeer BMP-4 mature part expressed from pTrcrd4/116. Mature part of reindeer BMP-4 is boxed. Cysteine residues typical for TGF-β superfamily are also marked by bold letters.

FIG. 6 shows amino acid (SEQ ID NO: 35) and nucleotide (SEQ ID NO: 36) sequences of reindeer BMP-4 mature part expressed from pETrd4/116. Mature part of reindeer BMP-4 is boxed. Cysteine residues typical for TGF-β superfamily are also marked by bold letters.

FIG. 7 shows amino acid (SEQ ID NO: 37) and nucleotide (SEQ ID NO: 38) sequence of recombinant reindeer BMP-4 mature part expressed from pIVEXrd4/116 plasmid. Mature part of reindeer BMP-4 is boxed. Cysteine residues typical for TGF-β superfamily are also marked by bold letters.

FIG. 8 shows a Coomassie stained SDS-PAGE of fractions eluted from HiTrap column (Example 3C). The bands represent 1) starting material, 2) flow through, 3) first wash, 4) second wash, 5) standard, 6) pH-gradient elution pH 6.2, 7) pH-gradient elution pH 5.3 and 8) pH-gradient elution pH 4.0. FIG. 9 shows X-ray images of a mouse hindquarter muscle: A) reference implanted with hBMP4 and B) implanted with BMP4 of the present invention.

Figure 1:
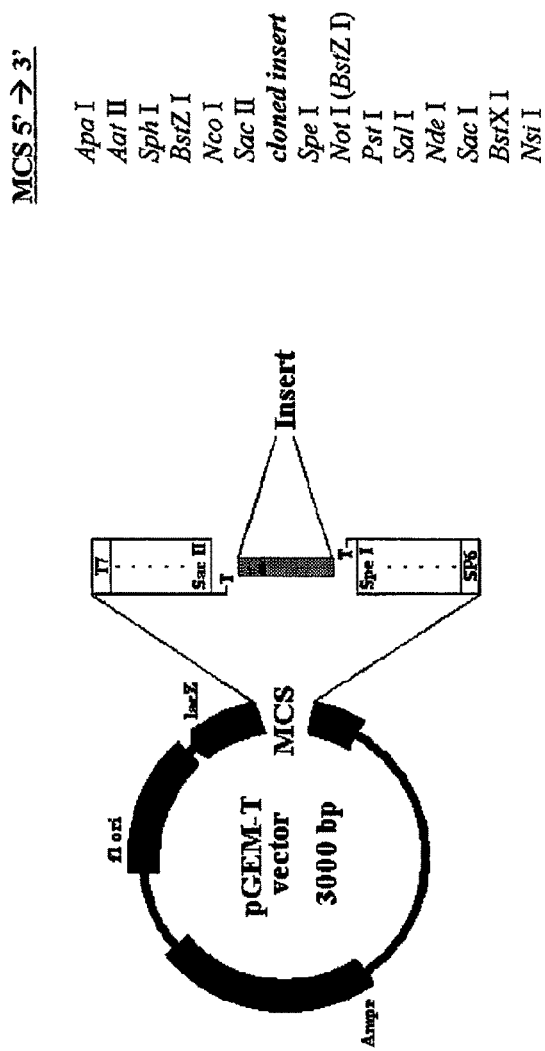
FIG. 1 shows plasmids containing rdBMP-4 inserts in PCR vector pGEM-T® (Promega).

mature part has the lowest homology (96%) with the rabbit counterpart. At the nucleotide level the homology between mature parts of reindeer and Texas fallow deer BMP-4 reached 99% and between reindeer and human 93%. When compared to reindeer BMP-4 mature part the lowest homology at nucleotide level was with rat 88%. Generally BMP-4 has homology also with other types of BMPs, for example with BMP-2.

TABLE 1

Homology of BMP-4 mature part of different mammalian origin at nucleotide and amino acid level presented as percentages (%).

| Origin | Reindeer | | Deer | | Human | | Mouse | | Rat | | Rabbit | | Dog | |
|---|---|---|---|---|---|---|---|---|---|---|---|---|---|---|
| | nt | aa | nt | aa | nt | aa | nt | aa | nt | aa | nt | aa | nt | aa |
| Reindeer | 100 | 100 | 99 | 99 | 93 | 98 | 89 | 98 | 88 | 98 | 93 | 96 | 94 | 98 |
| Deer | 99 | 99 | 100 | 100 | 93 | 99 | 89 | 99 | 89 | 99 | 94 | 97 | 95 | 99 |
| Human | 93 | 98 | 93 | 99 | 100 | 100 | 91 | 99 | 89 | 99 | 94 | 94 | 95 | 99 |
| Mouse | 89 | 98 | 89 | 99 | 91 | 99 | 100 | 100 | 95 | 100 | 89 | 96 | 89 | 98 |
| Rat | 88 | 98 | 89 | 99 | 89 | 99 | 95 | 100 | 100 | 100 | 88 | 96 | 89 | 98 |
| Rabbit | 93 | 96 | 94 | 97 | 94 | 94 | 89 | 96 | 88 | 96 | 100 | 100 | 94 | 96 |
| Dog | 94 | 98 | 95 | 99 | 95 | 99 | 89 | 98 | 89 | 98 | 94 | 96 | 100 | 100 |

(nt = nucleotides, aa = amino acids)

The following alignment shows the amino acid sequences of human and reindeer mature BMP-4 proteins (made with ClustalX 1.8 program (Thompson, J. D., Higgins, D. G. and Gibson, T. J. (1994) Nucleic Acids Research, 22: 4673-4680), rdBMP-4=reindeer BMP-4 (SEQ ID NO: 1), hBMP-4=human BMP-4 (SEQ ID NO: 2), the asterisks show the identical amino acids). These amino acid sequences differ only by two amino acids: amino acid 6 is serine in human and proline in reindeer (Ser6→Pro6), and amino acid 21 is leucine in human and proline in reindeer (Leu21→Pro21). Surprisingly the difference of only two amino acids leads to major differences in the function and efficiency of these two BMP-4 proteins. Since proline is a special amino acid generally having a strong effect to the structure and folding of proteins, it can easily be seen that the advantageous effect of the present invention is related to these specific two amino acids. Especially the proline 21 which replaces highly conserved leucine may play the major role in the present invention. Human BMP-4 is the closest counterpart of reindeer BMP-4 having the activity thereof determined.

```
rdBMP-4   SPKHHPQRARKKNKNCRRHSPYVDFSDVGWNDWIVAPPGYQAFYCHGDCPFPLADHLNST   (SEQ ID NO: 1)

hBMP-4    SPKHHSQRARKKNKNCRRHSLYVDFSDVGWNDWIVAPPGYQAFYCHGDCPFPLADHLNST   (SEQ ID NO: 2)
          *** .******** ************************************** rdBMP-4   NHAIVQTLVNSVNSSIPKACCVPTELSAISMLYLDEYDKVVLKNYQEMVVEGCGCR       (Cont'd of SEQ ID NO: 1)

hBMP-4    NHAIVQTLVNSVNSSIPKACCVPTELSAISMLYLDEYDKVVLKNYQEMVVEGCGCR       (Cont'd of SEQ ID NO: 2)
          ********************************************************
```

DETAILED DESCRIPTION OF THE INVENTION

Among mammalian species the homology of previously known BMP-4 mature parts is very high being 100% between mouse and rat. When these two mature parts are compared to their counterparts characterized from Texas fallow deer and human the homology is 99% (Table 1). Cloning and characterization of reindeer BMP-4 mature part revealed that at the amino acid level it has the highest homology with Texas fallow deer BMP-4 99% and 98% homology with mouse, rat, human and dog BMP-4. At amino acid level reindeer BMP-4

The "BMP-4 protein of the invention" or "bone morphogenetic protein of the invention" refers to a protein having bone morphogenetic (or morphogenic as both words are used interchangeably) activity, such as BMP-4 isolated from reindeer as described herein (SEQ ID NO: 1 of the attached sequence listing or rdBMP-4 in the alignment above), and includes homologues, analogs, derivatives and fragments thereof. Such homologues or derivatives include functional derivatives of said protein, such as proteins derived from the original reindeer BMP-4 protein or any BMP from any species. The derivatives may differ in length and they may contain amino acid insertions, deletions and substitutions, as a person skilled in the art well knows. Characteristic for the bone morphogenetic protein of the present invention are the essential amino acids 6 and/or 21 of the mature protein, which are both prolines in reindeer, as disclosed in the alignment above. Preferably the regions containing these amino acids are conserved in a BMP protein of the present invention.

On the other hand, insertions, deletions and substitutions located far outside said characteristic area may not be likely to cause substantial changes in the function, effect or folding of the BMP of the present invention. For example homologues having deletions, such as deletions of few amino acids, preferably 1-10 amino acids, more preferably 1-5 amino acids, most preferably 1-3 amino acids, in carboxyl terminus or amino terminus resulting in shorter polypeptide are in the scope of the present invention as long as said deletions do not affect the characteristic amino acids of the BMP of the invention. It is preferred that said homologues have the advantageous properties of the original reindeer BMP-4 proteins, said properties being related to said characteristic amino acids Pro6 and/or Pro21 and/or the region around it. Said homologues may have amino acid substitutions which do not substantially affect the function and effect of the protein of the invention. For example an amino acid not located in the active site or near it may be substituted with another amino acid having similar structural and/or chemical properties (e.g. hydrophobic or hydrophilic), i.e. conservative amino acid replacement, as long as said substitution does not substantially alter the function or folding of the mature protein. These kinds of substitutions are well known and understood in the art. Examples of such amino acid properties divided into groups are hydrophobic (Met, Ala, Val, Leu, Ile), neutral hydrophilic (Cys, Ser, Thr), acidic (Asp, Glu), basic (Asn, Gln, His, Lys, Arg), residues that influence chain orientation (Gly, Pro) and aromatic (Trp, Tyr, Phe) amino acids. Substitutions within said groups are generally not likely to cause major changes in the structure of the polypeptide backbone (e.g. a sheet or helical conformation), the charge or hydrophobicity of the molecule or the bulk of the side chain.

The homologues of the BMP (e.g. BMP-4) of the present invention include for example any known bone morphogenetic protein which contains or has been modified to contain at least one of said two essential amino acids, Pro6 or Pro21 or the corresponding amino acids in a homologous BMP in the case the numbering should differ. Also any currently unknown BMP-4 protein from any species modified as described above is in the scope of the invention.

Since Pro21 replaces highly conserved leucine, the BMP of the present invention contains amino acid proline corresponding to the Pro21 or prolines corresponding to both of the prolines at Pro6 and Pro21 defined from SEQ ID NO: 1 at corresponding locations. Said locations are calculated from the amino terminus of SEQ ID NO: 1, corresponding virtually to any mature BMP-4 protein. The sequence at the amino terminus may be SPKHH (as in SEQ ID NO: 1) or homologue thereof, as for example in human or reindeer or in other mammalian. Said locations may be defined by aligning the similar sequences of said homologues, derivatives or fragments with the sequence of SEQ ID NO: 1.

If there were any insertions or deletions of amino acids in the amino acid sequence of said homologue, derivative or fragment affecting the numbering, those should be taken into account when defining the location of said essential prolines, for example by aligning the sequences as described above and then defining the locations of said essential amino acids. However, any of said homologues, derivatives or fragments of the BMP-4 protein should substantially have the function and efficiency disclosed herein. Because all the known BMP-4 proteins are highly conserved (Table 1, at least 96% at amino acid level in mammals, or the alignment below), defining the location of said essential prolines is unambiguous, such as in the case of human BMP-4. Also, said locations can be easily defined also from other BPMs (see the alignment below). Generally such level of homology may be at least 70%, preferably 80%, more preferably 90% and most preferably 96% at the amino acid level.

In another embodiment the BMP of the present invention is any BMP-4 containing the consensus sequence of BMP-4 family between the two prolines: P-Q-R-A/S-R-K-K/R-N/K-K/R-N/H-C-R-R-H-S/A-P. In still another embodiment the BMP of the present invention is any BMP-4 containing the corresponding consensus sequence of BMP-4 and BMP-2 aligned together: P-Q-R-A/S-R/K-K/R-K/N/R/L-N/K-K/R/S-N/H/S-C-R/K-R-H-S/A-P. This consensus sequences have been defined from a sequence alignment of several BMP-4 and/or BMP-2 proteins from different species, such as shown in the ClustalX alignment below. Said consensus sequences correspond to the amino acids 6-21 of SEQ ID NO: 1. Also other consensus sequences may be defined, for example ones defining an area around the second proline (Pro21 in SEQ ID NO: 1), such as in another embodiment: C-R/K-R-H-S/A-P-Y-V-D-F-S-D or similar sequences differing in length, e.g. by 1-5 amino acids. Such consensus sequences may be defined from the alignment below or similar alignments made by aligning different related BMP proteins. The BMP sequences aligned are from reindeer (SEQ ID NO: 1), human (BMP-4: SEQ ID NO: 2, BMP-2: SEQ ID NO: 13), rabbit (SEQ ID NO: 3), bovine (SEQ ID NO: 4), dog (SEQ ID NO: 5), Texas fallow deer (Cervus dama, DAMDA, BMP-4: SEQ ID NO: 6, BMP-2: SEQ ID NO: 14), rat (SEQ ID NO: 7), mouse (BMP-4: SEQ ID NO: 8, BMP-2: SEQ ID NO: 15), house shrew (suncus murinus, SEQ ID NO: 9), chicken (SEQ ID NO: 10), African clawed frog (*Xenopus laevis*, BMP-4: SEQ ID NO: 11, BMP-2: SEQ ID NO: 16) and zebrafish (danio rerio, SEQ ID NO: 12).

In one embodiment the BMP of the invention is any BMP-2, such as reindeer BMP-2, which has been modified to contain the amino acids or a sequence, such as a consensus sequence, of the invention as described herein.

```
BMP4_REINDEER    SPKHHPQRARKKNKNCRRHSPYVDFSDVGWNDWIVAPPGYQAFYCHGDCPFPLADHLN    (SEQ ID NO: 1)

BMP4_HUMAN       SPKHHSQRARKKNKNCRRHSLYVDFSDVGWNDWIVAPPGYQAFYCNGDCPFPLADHLN    (SEQ ID NO: 2)

BMP4_RABBIT      SLKHHPQRARKKNKNCRRHALYVDFSDVGWNDWIVAPPGYQAFYCHGDCPFPLADHFN    (SEQ ID NO: 3)

BMP4_BOVINE      SPKHHPQRARKKNKNCRRHSLYVDFSDVGWNDWIVAPPGYQAFYCHGDCPFPLADHLN    (SEQ ID NO: 4)

BMP4_DOG         SPKHHAQRARKKNKNCRRHSLYVDFSDVGWNDWIVAPPGYQAFYCHGDCPFPLADHLN    (SEQ ID NO: 5)
```

```
                                      -continued
BMP4_DAMDA         SPKHHPQRARKKNKNCRRHSLYVDFSDVGWNDWIVAPPGYQAFYCHGDCPFPLADHLN     (SEQ ID NO: 6)

BMP4_RAT           SPKHHPQRSRKKNKNCRRHSLYVDFSDVGWNDWIVAPPGYQAFYCHGDCPFPLADHLN     (SEQ ID NO: 7)

BMP4_MOUSE         SPKHHPQRSRKKNKNCRRHSLYVDFSDVGWNDWIVAPPGYQAFYCHGDCPFPLADHLN     (SEQ ID NO: 8)

BMP4_SUNCUS        SPKHHPQRARKKNKNCRRHSLYVDFSDVGWNDWIVAPPGYQAFYCHGDCPFPLADHLN     (SEQ ID NO: 9)

BMP4_CHICKEN       SPKHHG-SRKNKKNCRRHALYVDFSDVGWNDWIVAPPGYQAFYCHGDCPFPLADHLN      (SEQ ID NO: 10)

BMP4_XENOPUS       SPKQQR-PRKKNKHCRRHSLYVDFSDVGWNDWIVAPPGYQAFYCHGDCPFPLADHLN      (SEQ ID NO: 11)

BMP4_ZEBRAFISH     SPKQRG---RKRNRNCRRHALYVDFSDVGWNDWIVAPPGYQAYYCHGECPFPLADHLN     (SEQ ID NO: 12)

BMP2_HUMAN         QAKHKQ-RKRLKSSCKRHPLYVDFSDVGWNDWIVAPPGYHAFYCHGECPFPLADHLN      (SEQ ID NO: 13)

BMP2_DAMDA         QAKHKQ-RKRLKSSCKRHPLYVDFSDVGWNDWIVAPPGYHAFYCHGECPFPLADHLN      (SEQ ID NO: 14)

BMP2_MOUSE         QAKHKQ-RKRLKSSCKRHPLYVDFSDVGWNDWIVAPPGYHAFYCHGECPFPLADHLN      (SEQ ID NO: 15)

BMP2_XENOPUS       QARHKQ-RKRLKSSCRRHPLYVDFSDVGWNDWIVAPPGYHAFYCHGECPFPLADHLN      (SEQ ID NO: 16)
                    . :::      ::  :   *:**. *******************:*:****:********:*

BMP4_REINDEER      STNHAIVQTLVNSVNSSIPKACCVPTELSAISMLYLDEYDKVVLKNYQEMVVEGCGCR     (Cont'd of SEQ ID NO: 1)

BMP4_HUMAN         STNHAIVQTLVNSVNSSIPKACCVPTELSAISMLYLDEYDKVVLKNYQEMVVEGCGCR     (Cont'd of SEQ ID NO: 2)

BMP4_RABBIT        STNHAIVQTLVNSVNSSIPKACCVPTELSAISMLYLDEYDKVVLKNYQEMVVEGCGCR     (Cont'd of SEQ ID NO: 3)

BMP4_BOVINE        STNHAIVQTLVNSVNSSIPKACCVPTELSAISMLYLDEYDKVVLKNYQEMVVEGCGCR     (Cont'd of SEQ ID NO: 4)

BMP4_DOG           STNHAIVQTLVNSVNSSIPKACCVPTELSAISMLYLDEYDKVVLKNYQEMVVEGCGCR     (Cont'd of SEQ ID NO: 5)

BMP4_DAMDA         STNHAIVQTLVNSVNSSIPKACCVPTELSAISMLYLDEYDKVVLKNYQEMVVEGCGCR     (Cont'd of SEQ ID NO: 6)

BMP4_RAT           STNHAIVQTLVNSVNSSIPKACCVPTELSAISMLYLDEYDKVVLKNYQEMVVEGCGCR     (Cont'd of SEQ ID NO: 7)

BMP4_MOUSE         STNHAIVQTLVNSVNSSIPKACCVPTELSAISMLYLDEYDKVVLKNYQEMVVEGCGCR     (Cont'd of SEQ ID NO: 8)

BMP4_SUNCUS        STNHAIVQTLVNSVNSSIPKACCVPTELSAISMLYLDEYDKVVLKNYQEMVVEGCGCR     (Cont'd of SEQ ID NO: 9)

BMP4_CHICKEN       STNHAIVQTLVNSVNSSIPKACCVPTELSAISMLYLDEYDKVVLKNYQEMVVEGCGCR     (Cont'd of SEQ ID NO: 10)

BMP4_XENOPUS       STNHAIVQTLVNSVNSSIPKACCVPTELSAISMLYLDEYDKVVLKNYQEMVVEGCGCR     (Cont'd of SEQ ID NO: 11)

BMP4_ZEBRAFISH     STNHAIVQTLVNSVNTNIPKACCVPTELSAISMLYLDETDRVVLKNYQEMVVEGCGCR     (Cont'd of SEQ ID NO: 12)

BMP2_HUMAN         STNHAIVQTLVNSVNSKIPKACCVPTELSAISMLYLDENEKVVLKNYQDMVVEGCGCR     (Cont'd of SEQ ID NO: 13)

BMP2_DANDA         STNHAIVQTLVNSVNSKIPKACCVPTELSAISMLYLDENEKVVLKNYQDMVVEGCGCR     (Cont'd of SEQ ID NO: 14)

BMP2_MOUSE         STNHAIVQTLVNSVNSKIPKACCVPTELSAISMLYLDENEKVVLKNYQDMVVEGCGCR     (Cont'd of SEQ ID NO: 15)

BMP2_XENOPUS       STNHAIVQTLVNSVNTNIPKACCVPTELSAISMLYLDENEKVVLKNYQDMVVEGCGCR     (Cont'd of SEQ ID NO: 16)
                   **************:.*********************  ::*******:*********
```

In another embodiment the BMP of the present invention is any BMP or a homologue, derivative or fragment thereof containing the amino acids 6-21 of SEQ ID NO: 1. In still another embodiment the BMP of the present invention is any BMP or a homologue, derivative or fragment thereof containing the amino acids 1-16 of the SEQ ID NO: 1. In still another embodiment the BMP of the present invention is any BMP or a homologue, derivative or fragment thereof containing the amino acids 16-23 of SEQ ID NO: 1. In still another embodiment the BMP of the present invention is any BMP or a homologue, derivative or fragment thereof containing the amino acids 1-23 of SEQ ID NO: 1. In still another embodiment the BMP of the present invention is a BMP-4 protein or a homologue, derivative of fragment thereof, such as one containing the amino acid sequence of SEQ ID NO: 1. The homologues, derivatives or fragments mentioned in these embodiments shall contain at least the amino acid Pro6 (i.e. the mutation L→P as shown in the alignment above), or both amino acids Pro6 and Pro21 as described above. Said homologues, derivatives or fragments do not include the known BMP-4 proteins as such, such as hBMP-4, since they do not contain said characteristic amino acids of the BMP-4 of the present invention. However, a known BMP-4 modified to contain at least one of said characteristic amino acids may be considered as such homologue, derivative or fragment.

Another embodiment of the present invention provides the BMP as described above with a heparin binding site (HBS). Generally this is an amino acid sequence capable of binding heparin. In one embodiment said heparin binding site is located at the amino terminus of said BMP, such as before the sequence of SEQ ID NO: 1 or functional homologue thereof. In one embodiment the heparin binding site contains amino acid sequence AKHKQRKRGT (SEQ ID NO: 17) or QAKH-KQRKRGT (SEQ ID NO: 18). Said heparin binding site may also be a functional homologue, derivative or fragment thereof. The heparin binding site improves the expression of the recombinant BMP protein and also enhances the biological activity thereof. Further, the heparin binding site significantly helps the expression of recombinant bone morphogenetic proteins in bacterial cells, such as *E. coli.*

One embodiment of the present invention provides a nucleic acid molecule, such as a DNA or RNA molecule, encoding said BMP of the invention. Because of the degeneracy of the genetic code there are a number of different nucleic acid sequences encoding the BMP of the invention. All such nucleic acid variants are in the scope of the present invention. Preferably said nucleic acid molecule is a DNA molecule. Examples of said DNA sequences are disclosed in FIGS. 5-7. One embodiment of the present invention provides a replicable vector containing the nucleic acid molecule described above in operative association with an expression control sequence thereof. Such vector may be used for producing recombinant BMP of the present invention in a suitable host system.

The nucleic acid encoding the BMP of the invention may be inserted into said replicable vector for cloning or for expression. Various vectors are publicly available. The vector may, for example, be in the form of a plasmid, cosmid, viral particle or phage. The appropriate nucleic acid sequence may be inserted into the vector by a variety of procedures. In general, DNA is inserted into an appropriate restriction endonuclease site(s) using techniques well-known in the art. Vector components may include for example one or more signal sequence(s), an origin of replication, one or more marker genes, an enhancer element, a promoter, and a transcription termination sequence. Construction of such suitable vectors containing one or more of these components employs standard ligation techniques which are well-known to a person skilled in the art.

Generally said BMP may be produced recombinantly by expressing in any suitable host cell, such as bacterial host cell. Such methods are well known in the art and they are described in literature. It is essential that the protein is folded properly during the expression and it contains the necessary post-translational modifications.

It is not always possible to express and purify certain proteins properly, for example because of solubility or refolding problems. Usually *E. Coli* can not make post-translational modifications typical for mammalian cell systems. However, the inventors of the present invention have produced recombinant reindeer BMP-4 mature part in *E. Coli* and after purification and refolding managed to prove it to be in biologically active form.

There are certain benefits when a protein, such as a BMP, is expressed in a bacterial host, such as *E. coli*. The protein generally shows lowered immunogenicity when compared to a similar protein expressed in for example yeast host. This may be useful later when the protein is utilized, for example administered as a medicament. *E. coli* produces proteins without modifications, such as glycosylation. This is particularly useful for proteins for which glycosylation is not a requirement, but which could be a problem if the protein is produced in other systems (e.g. yeast), which can over-glycosylate, or add inappropriate carbohydrates to the protein, which could lead to reduced or no activity of expressed protein and potentially create a risk of immunogenicity (Pedro de Noronha Pissarra: Recombinant DNA Proteins for the Biopharmaceutical Industry and the Future for *Escherichia coli*. Business Briefing Pharma Outsourcing, London, 2004).

One embodiment of the present invention provides a host cell containing the nucleotide molecule or the nucleotide vector described above. Suitable cells include all prokaryotic and eukaryotic cells which are able to express the protein of the invention. Such host cells are well known in the art and a person skilled in the art can easily choose a suitable one.

Another embodiment provides a BMP produced by culturing said cell to express said protein and by recovering said expressed protein from said host cell. Any suitable methods for recovering or isolating the protein may be used and such methods are well-known in the art.

The BMP of the invention may be used for treating disorders related to bone, cartilage, tendon or periodontal defects or diseases or the like wherein regeneration, repair or growth thereof is desired, or other diseases. The protein of the invention may also be used to heal wounds, such as burns, incisions and ulcers, and to related tissue repair and also for treatment of cancer, as disclosed in EP1131087. Since BMP proteins generally lack species specificity, the patient suffering from said defect may be any suitable animal, preferably mammal, such as human, and the BMP protein used for treatment may be of any suitable origin. The use of related BMP proteins for several types of therapeutical applications is well known in the art (see e.g. U.S. Pat. No. 6,245,889 and WO 98/51354).

"Disorders related to bone, cartilage, tendon or tooth defects" as used herein refers generally to any known disorder wherein bone, cartilage, tendon or periodontal healing or reconstruction, i.e. regeneration, is desired. Non-limiting examples of treatments of disorders related to bone, cartilage, tendon or periodontal defects or diseases or the like are regeneration, repair and growth of bone and periodontal tissue; regeneration, repair and growth of bone in mammals, such as human; treatment of abnormalities of bone formation or regeneration; wound healing, ectopic bone induction and healing of segmental bone defects in vertebrates; treatment of skeletal disorders and deformations; repair of large bone defects originating from trauma, excision of tumors or congenital malformations, reconstructing bone stocks worn off by an implanted endoprothesis in revision operations and healing delayed or non-united fractures; repair of bone and cartilage defects such as critical size defects, non-critical size defects, non-union fractures, segmental non-union of fractures; acute fractures, chondral defects, osteochondral defects, subchondral defects; local bone and cartilage formation; defects resulting from degenerative diseases; dental applications such as repair of periodontal tissues, alveolar bone, cementum, tooth root membrane, filling of the tooth root canal and improvement or enhancement of fixation of the dental implant. More examples of such disorders can be found in Ann Rheum Dis, Volume 62, 2003, 73-78: Reddy AH: Cartilage morphogenetic proteins: role in joint development, homoeostasis and regeneration.

Other diseases wherein the BMP of the present invention is useful are for example cancer, fibromyalgia, psoriasis and other dermatological disorders, and rheumatic disorders and the like. Examples of such cancers and methods and compositions for treating thereof are disclosed in EP 1131087.

In one embodiment the BMP of the present invention, such as BMP-4, may be provided, in any application described herein, together with one or more additional morphogenetic proteins, such as another BMP protein species or the like. Generally this provides a synergetic effect, as it is known in the art. Examples of other suitable BMP proteins are, but are not limited to, BMP-1, BMP-2, BMP-3, another BMP-4, BMP-5, BMP-6, BMP-7 and BMP-8. Also other therapeutically useful agents may be provided, such as epidermal growth factor, fibroblast growth factor and transforming growth factors (U.S. Pat. No. 6,245,889). In one embodiment said additional morphogenetic protein is originated from reindeer, such as any other reindeer BMP protein. In one embodiment the BMP-4 of the present invention is provided as a dimer, as a homodimer or as a heterodimer together with another BMP protein as described above. In still another embodiment the BMP-4 protein as a dimer or together with another factor or protein, as described above, is used for manufacturing medicament for treating disorders described in the specification.

In one embodiment of the present invention an osteogenic device, such as an implant, is provided containing the BMP of the invention. The osteogenic device may contain a biocompatible matrix, such as a calcium phosphate, carboxy methyl cellulose or collagen matrix or combinations thereof. In one embodiment said calcium phosphate matrix is a hydroxyapatite matrix. Said matrix may provide slow release of the BMP protein and/or the appropriate environment for presentation of the BMP protein. The osteogenic device may also contain a metal implant surrounded by said biocompatible matrix. One example of said metal is titanium. Some examples of such osteogenic devices are disclosed in WO 98/51354.

Non-limiting examples of the different framing materials, carriers or frames for forming e.g. different kinds of osteogenic devices or the like with the protein of the present invention are a medium in the form of powder, sponge, strip, film, gel, web or solution or suspension; semi-solid liquid carrier suitable for intramuscular, intravenous, intramedullary or intra-articular injection; isolated mesenchymal stem cells; any pharmaceutically acceptable vehicle; crusted auto- or allograft; any pharmaceutically acceptable matrix; a material selected from the group comprising hydroxyapatite, collagen, polymers (e.g. polylactic acid, polyglycolic acid), synthetic polymers, hyaluronic acid, α-BSM, calcium phosphate, tricalcium phosphate, aporous ceramic biopolymers, aporous resorbable biopolymers, coral, demineralized bone, bioglass, any biodegradable material and combinations thereof; binding agents selected from the group comprising mannitol, dextrans, white petrolatum, alkyl and methyl celluloses, wetting agents such as sodium salt, fobrin glue, mammalian fibrinogen and thrombin and combinations and admixtures thereof. The osteogenic device may be for example a structurally stable, three-dimensional implant in form of a cube, cylinder or block or in the shape of an anatomical form or an injectable form. Examples of osteogenic devices, useful materials and techniques are disclosed in book "Skeletal reconstruction and bioimplantation" (T. Sam Lindholm, 1997, Springer-Verlag, Heidelberg, Germany).

In one embodiment of the present invention a pharmaceutical composition is provided containing a therapeutically effective amount of BMP of the invention in a pharmaceutically acceptable vehicle or carrier. Said pharmaceutical compositions may be used for treating disorders related to bone, cartilage, tendon or periodontal defects or diseases, wounds and other tissue defects or any other disorders described herein.

One embodiment of the present invention provides a method for inducing the formation of bone, cartilage, tendon, tooth or the like wherein said bone, cartilage, tendon, tooth or the like is treated with the BMP of the invention or combinations thereof as described above, in vitro or in vivo. Still another embodiment of the invention provides a method for treating disorders described in the specification comprising administering the isolated BMP of the present invention to a patient suffering from said disorders. Said BMP may be administered as a pharmaceutical composition or as an osteogenic device described above. Further morphogenetic proteins or other useful agents may be administered together with said BMP of the invention, as described above, to enhance the therapeutical effect.

In the following description and examples it is described how recombinant reindeer BMP-4 mature part with heparin-binding site (HBS) according to embodiments of the present invention was produced in E. Coli. After purification and refolding the osteoinductive activity was verified by bioassay in mouse tight muscle pounches. The in vivo bioassay is a standard method used for assaying BMP activity since its discovery. It includes implantation of BMP in the hindquarter muscle of a mouse and estimation of heterotopic new bone induction after 10-21 days by radiology and histology.

In the following description and examples it is described how recombinant reindeer BMP-4 mature part according to one embodiment of the present invention was produced in E. Coli. After purification and refolding the osteoinductive activity was verified by bioassay in mouse tight muscle pounches. The in vivo bioassay is a standard method used for assaying BMP activity since its discovery. It includes implantation of BMP in the hindquarter muscle of a mouse and estimation of heterotopic new bone induction after 10-21 days by radiology and histology: Image analysis in determination of BMP activity is done by attenuation of X-ray beam through bone and it can be seen on the radiograph as an X-ray-positive "radioplaque" shadow compared to soft tissues. This is the basis for radiographic detection and radiomorphometric quantitation of newly formed bone after implantation of BMP or other bone inductive agent in a heterotopic or an orthotopic site.

The osteoinduction was observed in all three study groups (1 mg, 3 mg and 5 mg of recombinant reindeer BMP-4) and it was increased in dose-dependent manner (Table 2). When compared to its human counterpart the recombinant reindeer BMP-4 was verified to be about five times more potent bone inducer than identically produced recombinant human BMP-4 (even with 7.5 mg doses) therefore being a potent osteoinductive agent for clinical applications.

TABLE 2

The observed osteoinduction.

|  | 1 mg | | | | 3 mg | | | | 5 mg | | | |
|---|---|---|---|---|---|---|---|---|---|---|---|---|
| Reindeer | (+) | ++ | + | (+) | − | (+) | +++ | +++ | + | ++ | +++ | +++ |
|  | (+) | (+) | − | − | + | + | (+) | − | − | − | (+) | − |
|  | − | − | − | − | − | − | − | − | ++ | (+) | + | +++ |
|  | − | − | − | − | ++ | − | +++ | +++ | +++ | +++ | +++ | +++ |
|  |  |  |  |  | (+) | − | +++ | +++ | +++ | +++ | +++ | − |
| Human | (+) | − | (+) | − | − | − | − | − | − | − | + | − |

The results of the in vivo bioassay are shown in FIG. 9. FIG. 9A is a reference and 9B is a sample implanted with BMP-4 of the present invention. The bioassay was carried out as described in Marshall R. Urist, J. J. Chang, A. Lietze, Y. K. Huo, A. G. Brownell and R. J. DeLange (1987): Preparation and Bioassay of Bone Morphogenetic Protein and Polypeptide Fragments, Methods Enzymol 146: 294-312.

There were great difficulties to get recombinant rdBMP-4 mature part expressed in *E. coli* TOP10. Therefore, the inventors assumed that poor expression was caused by the high GC-content in N-terminal region of the mature part of rdBMP-4. Because heparin binding site (HBS), existing in the beginning of the reindeer BMP-2 mature part, is coded by nucleotide sequence with low GC-content, a construct in which this HBS sequence was added in front of the rdBMP-4 mature part sequence was created and this way the inventors managed to improve the expression of recombinant.

HBS located in the N-terminus of rdBMP-2 contains 10 basic amino acid residues and is reminiscent of known or postulated heparin-binding sites in other growth factors. It is possible that the interaction between protein with HBS and extracellular matrix might have an important effect on the establishment of morphogenetic gradients during development by limiting the free diffusion of a protein. Therefore, it was assumed that HBS could also improve the biological activity of recombinant rdBMP-4 by prolonging the duration of disappearance of protein from the implantation site.

EXAMPLES

Example 1

Cloning and Sequencing of Mature Part of the cDNA of Reindeer BMP-4

A. RNA Isolation

The antlers of a 3-year-old male reindeer are cut off and frozen in liquid nitrogen immediately after slaughtering. The frozen antlers are cut in 0.5 cm slices and stored at −70° C. Reindeer antler mRNA is isolated using the QuickPrep® Micro mRNA Purification Kit (Pharmacia Biotech). A part of the reindeer antler slice is cut in small spices (about 1 mm$^3$) and 0.1 g of this tissue is added to 0.6 ml of Extraction Buffer containing guanidinium thiocyanate and N-lauroyl sarcosine. The tissue is homogenized with Ultra Turrax for 3 times 10 seconds on ice and cooled between every homogenization. 1.2 ml of Elution Buffer is added and suspension is further homogenized for 1 times 10 seconds. A uniform suspension is obtained.

The reindeer antler homogenate and Oligo(dT)-Cellulose are centrifuged at top speed [14,000 rpm, RT, Centrifuge 5415 C (Eppendorf)] for 1 minute. The buffer from the Oligo (dT)-Cellulose pellet is removed and the cleared tissue homogenate is placed on the top of it. The tube is inverted to resuspend the Oligo(dT)-Cellulose pellet. The suspension is gently mixed for 5 minutes and centrifuged at top speed [14,000 rpm, RT, Centrifuge 5415 C (Eppendorf)] for 10 seconds. The supernatant is discarded.

Oligo(dT)-Cellulose is resuspended in High-Salt Buffer [10 mM Tris-HCl (pH 7.5), 1 mM EDTA, 0.5 M NaCl] and suspension is centrifuged at top speed [14,000 rpm, RT, Centrifuge 5415 C (Eppendorf)] for 10 seconds. Washings with High-Salt Buffer are repeated for 5 times and 2 additional times with Low-Salt Buffer [10 mM Tris-HCl (pH 7.5), 1 mM EDTA, 0.1 M NaCl]. 3 ml Low-Salt Buffer is added and suspension is transferred to MicroSpin Column. The MicroSpin Column is placed in Eppendorf tube and centrifuged at top speed for 5 seconds. Oligo(dT)-Cellulose in the column is rinsed for 3 times with Low-Salt Buffer.

The reindeer antler mRNA is eluted to a clean Eppendorf tube from the MicroSpin Column by adding 0.2 ml 65° C. Elution Buffer (QuickPrep® Micro mRNA Purification Kit, Pharmacia Biotech) to the column and centrifuging at top speed [14,000 rpm, RT, Centrifuge 5415 C (Eppendorf)] for 5 seconds. The elution step is repeated twice. The isolated mRNA is precipitated by adding 5 µl of glycogen solution (5-10 mg/ml in DEPC-treated $H_2O$), 1/10 volume potassium acetate solution (2.5 M potassium acetate, pH 5.0) and 0.5 ml absolute ethanol (chilled to −20° C.) to each elution. Precipitation is allowed to occur at −20° C. for at least 30 minutes and mRNA is centrifuged at top speed [14,000 rpm, 4° C., Centrifuge 5415 C (Eppendorf)] for 5 minutes. Precipitated mRNA is stored at −70° C. until cDNA synthesis is performed.

B. cDNA Synthesis

Reverse transcription of the reindeer antler mRNA is performed by modifying the instructions of the Time Saver™ cDNA Synthesis Kit (Pharmacia Biotech). 3 µg of mRNA is heat-denatured at 65° C. for 10 minutes and chilled on ice. 0.2 µmol DTT, 0.5 µg Oligo(dT)$_{12-18}$ Primer and heat-denatured mRNA are added to First strand reaction mix containing FPLCpure™ Cloned Murine Reverse Transcriptase, RNA-guard™, RNase/DNase-Free BSA, dNTPs (dATP, dCTP, dGTP and dTTP) in aqueous buffer (Time Saver™ cDNA Synthesis Kit, Pharmacia Biotech). The mixed solution is incubated at 37° C. for 1 hour. After the incubation, the First strand reaction mix is added to the Second strand reaction mix containing *E. coli* RNase H and *E. coli* DNA polymerase I and dNTPs in aqueous buffer (Time Saver™ cDNA Synthesis Kit, Pharmacia Biotech). The solution is mixed gently and incubated in RT for 30 minutes. The synthesized cDNA is stored at 4° C.

C. Screening of Reindeer Antler cDNA

The mature part of the cDNA of the reindeer BMP-4 is amplified by PCR (Polymerase chain reaction) method using primers (5'-GGATCCGAGCCCCAAGCATCACCCACA-GAGG-3' SEQ ID NO: 19) and (3'-AAGCTTGCGGCAC-CCACATCCCTCCACTAC-5' SEQ ID NO: 20) (Table 3) designed on the basis of homology of already known BMP-4 gene of Texas fellow deer. In addition to 100 ng of reindeer antler cDNA and 40 µmol of each primers the 50 µl of PCR reaction mixture contains 0.4 mM dNTPs (PCR Core Kit, Roche) and 0.7 U/µl Expand High Fidelity enzyme mix (thermostable Taq polymerase+proofreading polymerase, Roche) in Expand High Fidelity buffer with $MgCl_2$ (Expand High Fidelity PCR System, Roche). The reaction is performed under the following program using Mastercycler personel apparatus (Eppendorf): initial denaturation at 94° C. for 4 minutes and 25 cycles of denaturation 94° C. for 1 minute, annealing of the primers 55° C. for 1 minute, elongation of DNA strands 72° C. for 2 minutes. The final extension is performed at 72° C. for 10 minutes.

TABLE 3

Primers used in cloning of the mature part of reindeer BMP-4

```
Primers for cloning
mature cDNA part of reindeer BMP-4
for      5' → 3'  GGATCCGAGCCCCAAGCATCACCC ACAGAGG
pTrcHis           (SEQ ID NO: 19)
2A       3' → 5'  AAGCTTGCGGCACCCACATCCCTCCACTAC
                  (SEQ ID NO: 20)

for      5' → 3'  CCGCGGTAGCCCCAAGCATCACCCACAGAGG
pIVEX2.4          (SEQ ID NO: 21)
         3' → 5'  GGATCCTAGCGGCACCCACATCCCTCCACTAC
                  (SEQ ID NO: 22)
```

D. Cloning into pGEM®-T Vector

The PCR products were purified straight from the PCR reaction mix by Wizard® PCR Preps DNA Purification System (Promega) and ligated into the pGEM®-T vector (FIG. 1) by T4 DNA Ligase (PGEM®-T Vector System I; Promega). 0.3 μg of purified PCR product and 2.3 μg/ml of pGEM®-T vector are added to ligation buffer containing 18 mM Tris-HCl (pH 7.8), 6 mM MgCl$_2$, 6 mM DTT, 0.3 mM ATP, 3% polyethylene glycol and 0.14 U/μl T4 DNA Ligase in total volume of 66 μl. The reaction is allowed to occur at +16° C. water bath which is allowed to cool down to +4° C. overnight. The newly formed plasmid is called pGEMrd4/116 (FIG. 1).

E. The Production of Competent *Escherichia Coli* TOP10 F' Cells

The competent *Escherichia coli* TOP10 F' cells (Invitrogen) are produced by the calcium chloride/magnesium chloride procedure. 2 ml of LB-medium is inoculated with *E. coli* TOP10 F' cells and grown overnight at 37° C. with shaking (225 rpm). Next morning 100 ml of fresh LB-medium is inoculated with 1 ml of overnight culture and the culture is grown at 37° C. with shaking (225 rpm) to an OD$_{600}$=0.5-0.6. The cultured cells are collected by centrifugation (2500×g, 5 min), resuspended in 10 ml of 0.1 M MgCl$_2$ solution and collected again by centrifugation (2500×g, 5 min). After the MgCl$_2$ treatment the cells are resuspended in 10 ml of 0.1 M CaCl$_2$ solution, incubated in ice bath for 30 minutes and recollected by centrifugation (2500×g, 5 min). The CaCl$_2$ treatment is repeated except in the second time 3.5 ml of CaCl$_2$ is used and the incubation time is 1 hour. Glycerol is added to suspension to final concentration of 14% (v/v) and the solution is divided into 200 μl portions. The competent *E. coli* TOP10 F' cells are frozen in liquid nitrogen and stored at −70° C.

F. Transformation of the Competent *Escherichia Coli* TOP10 F' Cells and Selection of Clones Containing Reindeer BMP-4

The competent *Escherichia coli* TOP10 F' cells are melted in ice bath for 15 minutes. 10 μl of ligation mix (described above) is added to 100 μl of TCM (10 mM Tris-HCl, 10 mM CaCl$_2$, 10 mM MgCl$_2$, pH 7.0) and mixed with 200 μl of the competent *E. coli* cells. The mixture is incubated in ice bath for 30 minutes before the heat shock (43° C., 3 minutes). After the heat shock 800 μl of LB medium is added and the cells are allowed to regenerate for 45 minutes at 37° C. The transformed cells are collected by centrifugation at top speed for 2 minutes and resuspended to 30 μl of growth medium. The cell suspension is plated to two LB plates containing 25 μg/ml ampicillin covered with 1 mmol IPTG (isopropyl-β-D-thiogalactopyranoside) and 2.4 nmol X-gal (5-bromo-4-chloro-3-indolyl-β-D-galactoside) and the cells were grown at the plates overnight at 37° C. The positive clones are recognized as white colonies based on α-complementation of lacZ gene. The method is described in detail in Sambrook and Russel (2001), Molecular Cloning, Cold Spring Harbor Laboratory Press, New York.

G. Isolation of pGEMrd4/116 Plasmids and Sequencing of cDNA Inserts

The plasmids are isolated by Wizard® Plus Minipreps DNA Purification System (Promega) and then further purified by ethanol precipitation. The cDNA identity is confirmed by sequencing with ABI Prism (Perkin-Elmer Corporation). The sequencing reaction is performed using DYEnamic ET Terminator Cycle Sequencing Kit (Amersham Pharmacia Biotech) and Mastercycler Personel apparatus (Eppendorf). The primers in the PCR reaction for sequencing are (5'-TAATAC-GACTCACTATAGGGCGA-3' SEQ ID NO: 23) and (3'-ATTTAGGTGACACTATAGAATAC-5' SEQ ID NO: 24) (Table 4) and the program is as follows: 25 cycles of denaturation 94° C. for 30 seconds, annealing 50° C. for 15 seconds, elongation for 60° C. The amplified PCR products are precipitated by ethanol precipitation method. In 10 μl reaction 1 μl of 1.5 M Na-acetate—250 mM EDTA buffer and 95-100% ethanol is added so that the final ethanol concentration is 75%. The precipitation is allowed to occur in ice bath for 10 minutes and then the mixture is centrifuged for 20 minutes. The supernatant is discarded and the pellet is washed with 125 μl of 70% ethanol in RT. The solution is centrifuged briefly and the washing ethanol is removed as precisely as possible. The pellet is dried in 37° C. for a few minutes until all the ethanol is completely fumed. The ABI Prism apparatus located in Department of medical biochemistry and molecular biology, University of Oulu, Finland, was used for the final sequencing.

TABLE 4

Primers used in sequencing on the mature part of reindeer BMP-4

| Primers for sequencing | | | |
|---|---|---|---|
| pGEM-T ® plasmids | 5' → 3' | | TAATACGACTCACTATAGGGCGA (SEQ ID NO: 23) |
| | 3' → 5' | | ATTTAGGTGACACTATAGAATAC (SEQ ID NO: 24) |
| pTrcHis2A plasmids | 5' → 3' | | AGAGGTATATATTAATGTATCG (SEQ ID NO: 25) |
| | 3' → 5' | | ATGGTCGACGGCGCTATTCAG (SEQ ID NO: 26) |
| pIVEX2.4c plasmids | 5' → 3' | | TAATACGACTCACTATAGGGCGA (SEQ ID NO: 27) |
| | 3' → 5' | | GCTAGTTATTGCTCAGCGG (SEQ ID NO: 28) |

Example 2

Expression of the Recombinant Reindeer BMP-4 Mature part in *Escherichia coli* TOP10 F', Origami B (DE3) and Rosetta (DE3) Cells A. Subcloning of the Mature Part of Reindeer BMP-4 from pGEM®-T vector to the Expression Vector pTrcHis 2A (Invitrogen) and Transformation of the Competent *Escherichia Coli* TOP10 F' Cells The subcloning of the mature part of reindeer BMP-4 from pGEM®-T vector to the expression vector pTrcHis 2A (FIG. 2) is accomplished by first digesting the mature part off from pGEM®-T vector using Bam HI and Hind III restriction enzymes and then ligating the insert to pTrcHis 2A digested with the same enzymes. The Bam HI (Roche) and Hind III (Roche) digestion of pGEM®-T construct and pTrcHis 2A (1 μg) is performed in 10 μl of 10 mM Tris-HCl, 10 mM NaCl, 5 mM MgCl$_2$, 1 mM 2-mercaptoethanol, pH 8.0 (SuRE/Cut Buffer B, Roche) with 1 U/μl of each restriction enzyme. The reaction is allowed to occur for 1.5 hours in 37° C. and then the restriction enzymes are inactivated by heating in 65° C. for 20 minutes and freezing in −20° C. Ligation is performed in 2× Rapid Ligation Buffer (supplied with pGEM®-T vector by Promega) in +16° C. water bath which is allowed slowly to cool to +4° C. overnight (ligase concentration 0.1 U/μl).

Figure 2:
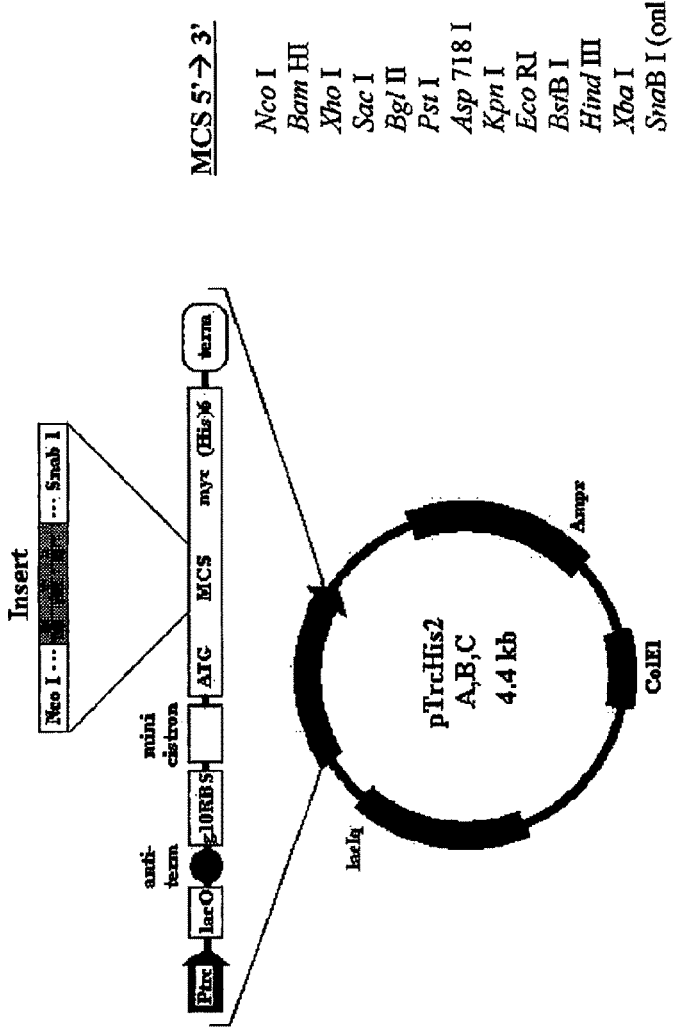
FIG. 2 shows plasmids containing rdBMP-4 inserts in expression vector pTrcHis2A (Invitrogen).

The newly formed construct is checked by sequencing (protocol is described in Example 1 Part G) using primers (5'-AGAGGTATATATTAATGTATCG-3' SEQ ID NO: 25) and (3'-ATGGTCGACGGCGCTATTCAG-5' SEQ ID NO:

26). Expression vector containing pTrcHis 2A plus the reindeer BMP-4 mature part cDNA is named as pTrcrd4/116 (FIG. 2). The competent *Escherichia coli* TOP10 F' cells are transformed as described in Example 1 Part F.

Figure 3:
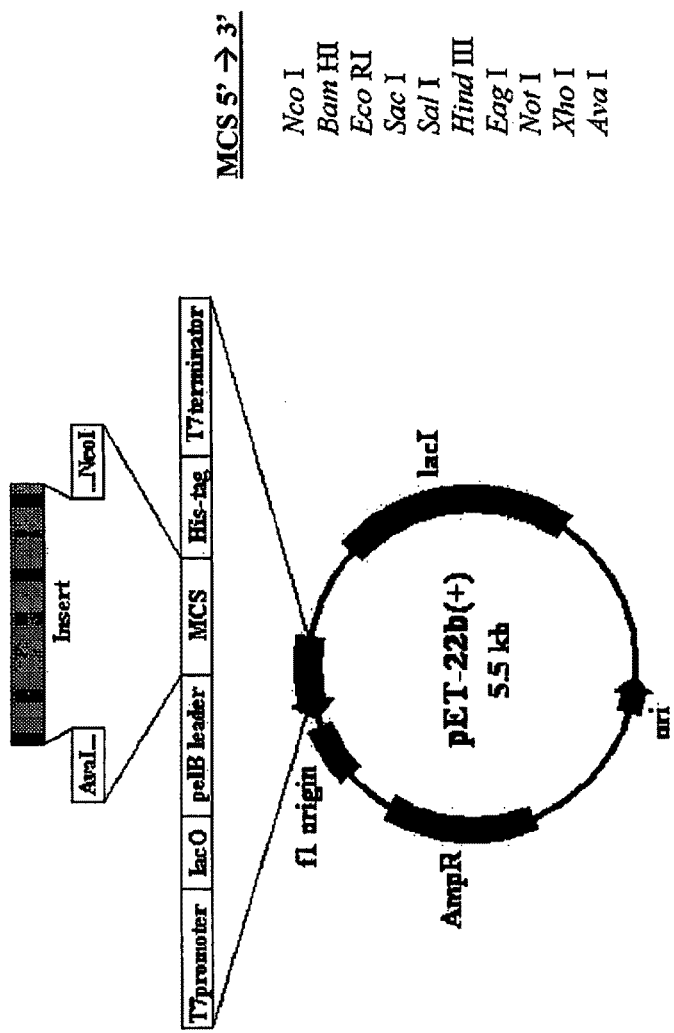
FIG. 3 shows plasmids containing rdBMP-4 inserts in expression vector pET-22b(+) (Novagen).

B. Insertion of the Mature Part of Reindeer BMP-4 to the Expression Vector pET22b(+) (Novagen) and Transformation of the Competent *Escherichia coli* Origami B (DE3) and Rosetta (DE3) Cells The subcloning of the mature part of reindeer BMP-4 to the expression vector pET22b(+) (Novagen) (FIG. 3) is performed as described above (see Example 2 Part A). The newly formed plasmids containing pET22b(+) plus the reindeer BMP-4 mature part cDNA is named as pETrd4/116 (FIG. 3). The competent *Escherichia coli* Origami B (DE3) (Novagen) and Rosetta (DE3) (Novagen) cells are transformed following the instructions of the user manual shipped with the competent cells (Novagen).

C. Expression of the Recombinant Reindeer BMP-4 Mature Part in *Escherichia coli* Cell Cultures and Collection of the Cells

*E. coli* cells [TOP10, Origami B (DE3) and Rosetta (DE3)] containing either pTrcrd4/116 or pETrd4/116 are grown overnight in 50 ml of SOB medium containing ampicillin (50 µg/ml) and for Rosetta (DE3) cells also chloramphenicol (35 µg/ml) in +37° C. with shaking (225 rpm). Next morning 1200 ml of SOB medium, containing antibiotics mentioned above, is inoculated with 24 ml of overnight culture and incubated in +37° C. with shaking (225 rpm) until $OD_{600}$ is 0.6 when the cells are in mid-log phase. At this point the recombinant protein expression is induced by adding IPTG to final concentration 1 mM. After the induction the cells are grown additional 4 to 5 hours and then collected by centrifugation. The amino acid sequences of the recombinant proteins produced with respective nucleotide sequences are presented in FIG. 5 (pTrcrd4/116) and FIG. 6 (pETrd4/116).

Example 3

Purification and Refolding of the Recombinant Reindeer BMP-4 Mature Part

A. Washing of Inclusion Bodies

Collected cells are suspended in 50 mM Na-phosphate buffer (pH 7.0, 220 g cells/1 liter of buffer) by shaking. Suspension is centrifuged in 5,500 g for 45 minutes in +4° C. Na-phosphate washing is repeated once. Cell pellet is weighted and stored in −70° C. overnight. Frozen pellet with partly erupted cells is thawed and suspended in 20 mM Tris-HCl buffer with 0.5 mM EDTA (pH 8.5, 25 mg/ml) by shaking 2 minutes. Suspension is centrifuged 26,000 g for 30 minutes in +4° C. and Tris-HCl-EDTA washing is repeated once. The remaining pellet is weighted. In last washing step, pellet is suspended (200 rpm/minute, overnight, RT) in lysis buffer 6 M GuHCl—20 mM Na-phosphate—0.5 M NaCl (pH 8.0, 35 mg/ml) when all the remaining intact *E. coli* cells are erupted and inclusion bodies made soluble. Suspension is centrifuged (26,000 g, 45 min, RT), pellet discarded and recombinant protein in soluble form in remaining supernatant. Finally, to be sure to get rid of all cell remnants, supernatant is filtered through 45 µm filter.

B. Precipitation According to Isoelectric Point (pI)

The recombinant reindeer BMP-4 expressed from pETrd4/116 in *Escherichia coli* Origami B (DE3) or Rosetta (DE3) cells is precipitated by isoelectric precipitation in pH 8.12. Isoelectric point is determined with computer calculations according to amino acid sequence of the recombinant reindeer BMP-4 (FIG. 6). The precipitant is collected by centrifugation (12,000 g, 30 min, RT) and resuspended in lysis buffer (6 M GuHCl—20 mM Na-phosphate—0.5 M NaCl; pH 8.0).

C. Immobilized Metal Affinity Chromatography (IMAC)

*Escherichia coli* cells were lysed by shaking in 6 M GuHCl—20 mM Na-phosphate—0.5 M NaCl (pH 8.0) for 2 hours and filtrated through 45 µm filter. In IMAC method, pre-packed HiTrap Chelating HP affinity columns (Amersham Pharmacia Biotech) are used. Columns are charged with $Co^{2+}$, $Cu^{2+}$ or $Ni^{2+}$ ions according to instruction manual applied by supplier. The aid of the use of the his-tag-epitope at the end of the rdBMP-4 protein was that the his-tag-epitope bound up in the metal ion charged column and the impurities caused from *E. coli* cell debris flow through. After column charging, filtered supernatant from washing steps is applied in column. Majority of impurities is removed by washing the column with lysis buffer (6 M GuHCl—20 mM Na-phosphate—0.5 M NaCl, pH 8.0) 5-10 times the bed volume. Second washing is performed with 5-10 times the bed volume of buffer in which 6 M GuHCl of lysis buffer is replaced by 6 M urea. Recombinant reindeer BMP-4 is eluted from the HiTrap column by pH gradient from pH 7.0 to pH 4.0 (6 M urea—20 mM Na-phosphate—0.5 M NaCl). The fractions are analyzed by SDS-PAGE and the ones containing approximately pure rdBMP-4 are combined for refolding of recombinant protein (FIG. 8).

D. Refolding of Recombinant rdBMP-4 Mature Part

The BMP-4 fractions analyzed by SDS-PAGE were pooled and dialyzed against water. After dialysis precipitated protein was collected by centrifugation and resuspended in 8 M Urea, 0.1 M Tris/HCl, pH 8 in the presence of 100 mM DTT, 1 mM EDTA and incubated for 2 h at 25 degrees. The pH was lowered to pH 3-4 by drop wise addition of 1 M HCl. The DTT was removed completely by dialysis against 6 M urea, 10 mM HCl for 2 h at 25 degrees. Dialysis was continued at 4° C. overnight against 6 M urea. Refolding of recombinant rdBMP-4 was performed by two step dialysis. The first dialysis solution was 20 mM Tris-HCl—150 mM NaCl—3 M urea (pH 7.5). The dialysis buffer was changed for four times within two or three days. In second step all salts were removed by exhaustive water dialysis. Dialysis water was changed at least six times during two to three days. Desalted sample was centrifuged and pellet was dried by lyophilization. At that point the purity of BMP-4 was 75% and its refolding measured by non-reducing SDS-PAGE was 50%. Quantification of the refold dimer of recombinant reindeer BMP-4 on Coomassie Brilliant Blue stained gels was done densitometrically.

Example 4

The Biological Activity Test of the Recombinant Reindeer BMP-4 Mature Part

The biological activity of the lyophilized recombinant reindeer BMP-4 was tested by implanting less than one mg of recombinant protein absorbed into Lyostrypt® collagen sponge or gelatin capsule in mouse tight muscle pouches. BSA was used as control. The hind legs were roentgenographed and the implant sites dissected and fixed in 10% neutral formalin solution. Fixed implants were cut into 4 µm sections and stained with hematoxylin-eosin staining. Sections were examined with a light microscope. A new bone formation as an area and optical density was evaluated by radiographs. The radiographic images were transferred into a computer by using an optical scanner (HP Scan Jet, Hewlett Packard, USA). Ectopic and orthopic new bone formations were evaluated as the areas (mm$^2$) of calcified tissue visible in the radiographs defined by using the Scion Image Beta 4.02 (Scion Corp., USA) software. The mean optical density (mmAl) of the defined area was measured with the same equipment. Calibration of the optical density was performed by using an aluminum wedge (Al) with 0.25 mmAl steps, giving a calibrated density range up to 4 mmAl.

Example 5

Expression of the Recombinant Reindeer BMP-4 Mature Part in Rapid Translation System RTS 500

A. Construction of the RTS 500 Expression Vector pIVEX 2.4c (Roche)

Figure 4:
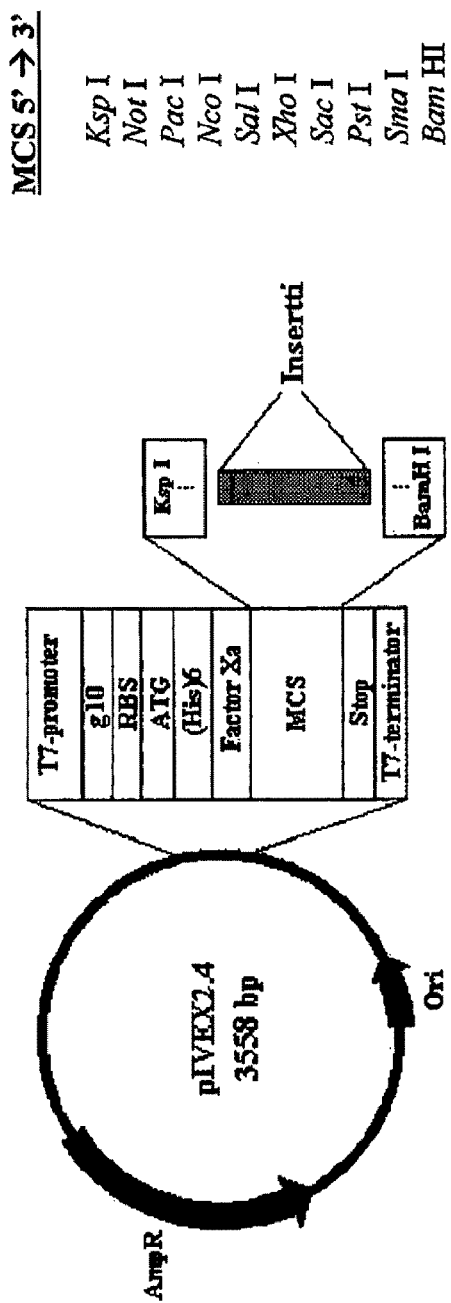
FIG. 4 shows plasmids containing rdBMP-4 insert in RTS500 expression vector pIVEX2.4c (Roche).

The amplification of the natural mature part of reindeer BMP-4, purification of the PCR product, the ligation into pGEM®-T vector (FIG. 1), the competent *Escherichia coli* TOP10 F' cell transformation, plasmid purification and the sequencing of the inserts are performed the same way as described in Example 1 except the primers for amplification of the mature part of reindeer BMP-4 are (5'-CCGCGG-TAGCCCCAAGCATCACCCACAGAGG-3' SEQ ID NO: 21) and (3'-GGATCCTAGCGGCACCCACATCCCTC-CACTAC-5' SEQ ID NO: 22) (table 2) and the construct is named pGEMrd4/116/2 (pMU5/2) (FIG. 1). Primers for sequencing the construct are (5'-TAATACGACTCACTAT-AGGGCGA-3' SEQ ID NO: 23) and (3'-GCTAGTTAT-TGCTCAGCGG-5' SEQ ID NO: 28) (table 4). In amplification primers there are recognition sites for restriction enzymes Ksp I (Sac II) and Bam HI at the 5' and 3' end of primers, respectively, and they are utilized in subcloning of the mature part of reindeer BMP-4. Plasmids pGEMrd4/116/2 and pIVEX 2.4c (0.5 µg) are digested in 10 µl volume of 10 mM Tris-HCl, 10 mM MgCl$_2$, 1 mM dithioerythritol, pH 7.5 (SuRE Cut Buffer L, Roche) with 1 U/µl of each restriction enzyme. The restriction enzymes are inactivated before the ligation and the ligation reaction is performed as described in Example 2 Part A. The newly formed construct is named as pIVEXrd4 (pMU500) (FIG. 4).

B. Production of the Recombinant BMP-4 Mature Part in RTS 500

The RTS 500 reaction is performed following the instructions of Rapid Translation System RTS 500 *E. coli* Circular Template Kit Instruction Manual. The amino acid sequence of the recombinant protein with respective nucleotide sequence is presented in FIG. 7.

Example 6

Addition of Heparin Binding Site in Front of the Mature Part of the Reindeer BMP-4

A. Addition of Heparin Binding Site Coding DNA Fragment to pTrcHis 2A Vector

Two complementary primers seen in Table 5 (5'→3': SEQ ID NO: 29, 3'→5': SEQ ID NO: 30) were designed using heparin binding site (HBS) of the reindeer BMP-2 as a model. Bam HI and Kpn I restriction sites were added in 5' and 3' ends of HBS, respectively. The primers were first denatured in +100° C. for 5 min and then annealed by allowing a small +100° C. water bath to cool down to room temperature and further to +4° C. (1h). Both annealed HBS fragment (1 µg) and pTrcHis 2A vector (0.5 µg) were digested by Bam HI (1 U/µl) and Kpn 1 (2 U/µl) in Multi-Core buffer (Promega) in +37° C. for 1.5 hours and ligated in +16° C. water bath which was allowed to cool down to +4° C. overnight. The newly formed construct was checked by sequencing (see Example 1 Part G) and named pTrcHBS (FIG. 2).

TABLE 5

Primers used in cloning of heparin binding site

Primers for HBS cloning

| 5' → 3' | CGGGATCCGCAAGCAAAACATAAACAGCGCAAACGCGGTACCCC (SEQ ID NO: 29) |
|---|---|
| 3' → 5' | GGGGTACCGCGTTTCCGCTGTTTATGTTTTGCTTGCGGATCCCG (SEQ ID NO: 30) |

B. Amplification of the Mature Part of BMP-4 and Cloning it into pGEM®-T-Vector

Kpn I restriction sites were created in front of the mature parts of rdBMPs with PCR method. Templates in these reactions were reindeer BMP cDNA cloned in pTrcHis2A vector between Bam HI and Hind III restriction sites (Example 2 Part A). Primers (Sigma-Genosys) designed for these reactions are shown in table 6.

TABLE 6

Primers used in PCR reaction creating KPN I and Hind III restriction sites in BMPs

| gene | primer |
|---|---|
| BMP-4/116 5' | 5' CAGGTACCAGCCCCAAGCATCACCCACAG 3' (SEQ ID NO: 31) |
| 3' | 5' AAGCTTGCGGCACCCACATCCCTCCAC 3' (SEQ ID NO: 32) |

PCR reactions were done with Expand High Fidelity System (Roche). Reactions contained: HF buffer, 1.5 mM MgCl$_2$, 200 µM dNTP mix, 0.8 µM both oligos, 15 ng template DNA and 3.5 U High Fidelity Enzyme mix. Program used in reactions was: 94° C. 4 min, 25 cycles; 94° C. 1 min, 55° C. 1 min, 72° C. 2 min, one cycle; 72° C. 10 min and temperature was lowered to 4° C.

Sizes of the PCR products were examined on 1% agarose gels. Standard used in gels was either 500 µg of 100 bp Ladder (BioLabs) or 100 bp Ladder XIV (Roche). One fifth of the PCR reactions were loaded in agarose gels with Bromphenol Blue DNA loading puffer. Samples were run in 1×TAE buffer (40 mM Tris, 10 mM sodium acetate, 1 mM EDTA pH 7.8) with 70 V for 35 min and pictures of the gels were taken under UV-light.

PCR products were purified from 1% SeaPlague®GTG® low melting temperature agarose (BioProducts) with Wizard® PCR Preps DNA purification system (Promega) according to manufactures protocol.

Purified DNA fragments from PCR reactions were ligated in pGEM®-T vector with pGEM®-T and pGEM®-T Easy Vector System (Promega). Reactions contained; Rapid Ligation buffer, 50 ng pGEM®-T vector, 15-20 ng of insert DNA and 3 U T4 DNA Ligase. Ligations were performed in 16° C. water bath which was allowed to cool down to 4° C. slowly overnight.

Before transformation ligation-mixes were digested with 15 U Bam HI (Roche) in B-buffer (Roche) to remove possible traces from PCR reaction template (BMP in pTrcHis2A). Digestion reactions were incubated 1.5 h in 37° C.

C. Transformation of Plasmids into *E. coli* TOP10 Cells

Plasmids were transformed into competent *Escherichia Coli* TOP10 cells (Invitrogen). TOP10 cells were made competent with calcium chloride/magnesium chloride procedure (see Example 1 part E).

Transformation of plasmids was performed as follows: digested lig-mix was mixed in 100 µl of TCM and added to 200 µl of competent TOP10 cells. Cells were incubated first 30 min on ice and then 3 min at 43° C. 0.8 ml of LB-glucose medium was added to cells and mixed by inverting the tube. Cells were left to grow for 45 min at 37° C. and plated on LB-glucose+AMP+IPTG+X-GAL plates.

Colonies from transformations were inoculated in 5 ml of LB-glucose+100 µl/ml ampicillin medium and grown overnight at 37° C. with shaking. Plasmids were isolated from overnight cultures with Wizard® Plus Minipreps DNA purification system (Promega) according to manufactures procedure.

Plasmids were further purified with EtOH precipitation: 5 µl of 3 M sodium acetate pH 5.8 and 150 µl of absolute ethanol was added to purified plasmids in water and DNA was left to precipitate at −20° C. overnight. In the next morning reactions were centrifuged in microcentrifuge 14000 rpm at 4° C., supernatant was removed and precipitated DNA was washed with 500 µl of cold 70% EtOH. Samples were centrifuged again and washing step was repeated. DNA was air dried and resuspended in 20 µl of sterile water.

Nucleotide sequences of the inserts were checked with sequencing. Sequencing reactions contained 5 µM of both primers and 150-300 ng of plasmid DNA. Sequencing primers are shown in table 6.

TABLE 7

| Sequencing primers for pGEM ®-T plasmids | |
|---|---|
| 5' primer | TAATACGACTCACTATAGGGCGA (SEQ ID NO: 23) |
| 3' primer | ATTTAGGTGACACTATAGAATAC (SEQ ID NO: 24) |

D. Addition of the mature part of reindeer BMP-4 to pTrcHBS and transformation the competent *Escherichia Coli* TOP10 F'

HBS sequence has previously been cloned into pTrcHis2A vector between Bam HI and Kpn I restriction sites (Example 6 part A). Before ligation, plasmid pTrcHBS as well as BMP-4 in pGEM®-T were first digested with Kpn I and Hind III enzymes. BMP in pGEM®-T Kpn I digestion reactions contained 800 ng of plasmid DNA, 2×L buffer (Roche), 150 ng of BSA and 20 U of Kpn I (Roche). pTrcHBS Kpn I digestion reactions contained 250 ng of plasmid DNA, 2×L buffer (Roche), 150 ng of BSA and 20 U of Kpn I (Roche). Reactions were incubated at 37° C. for 3 h. B buffer (Roche) and 10 U of Hind III (Roche) were added to the reactions and reactions were further incubated at 37° C. for 1 h 30 min.

Ligation reactions contained Rapid Ligation buffer (Promega), 125 ng of double digested pTrcHBS vector, 400 ng of double digested BMP in pGEM®-T and 3 U of T4 DNA Ligase (Promega). Ligations were performed in 16° C. water bath which was allowed to cool down to 4° C. slowly overnight. Ligation-mixes were digested in 1×H buffer (Roche) with 10 U of Pst I (Roche) and 12.5 U of EcoR I (Roche) to remove intact BMP in pGEM®-T and pTrc HBS plasmids. Reactions were incubated 1 h 30 min at 37° C.

BMP-4 in pTrcHBS plasmid was transformed into competent *E. coli* TOP10 cells, amplified, purified and sequenced in the same way as described for pGEM®-T plasmids earlier. Sequencing primers for pTrcHis2A plasmids are shown in table 8. The new constructs were named pTrcHBSrd4 (FIG. 2) in TOP10 cells and were stored as glycerol stocks at −70° C. Glycerol stocks were made according to manufactures protocol (Invitrogen).

TABLE 8

| Sequencing primers for pTrcHis2A plasmids | |
|---|---|
| 5' primer | AGAGGTATATATTAATGTATCG (SEQ ID NO: 25) |
| 3' primer | ATGGTCGACGGCGCTATTCAG (SEQ ID NO: 26) |

E. Expression of the Recombinant Reindeer BMP-4 Mature Part with Heparin Binding Site in *Escherichia coli* TOP10 Cell Cultures A pilot expression tests were done as follows; 2 ml of SOB medium containing 50 µg/ml ampicillin was inoculated with single recombinant TOP10 colony. Cells were grown overnight at 37° C. with shaking (225 rpm). In the morning 20 ml of fresh SOB medium with 50 µg/ml ampicillin was inoculated with 0.4 ml of overnight culture and cells were grown at 37° C. with shaking until $OD_{600}$ reached 0.6.

IPTG was added to a final concentration of 1 mM to induce the protein production in the cells. After induction cells were grown for 5 h at 37° C. with shaking. 0.5 ml samples were collected from culture at time points of 0 h, 1 h, 2 h, 3 h, 4 h, and 5 h after induction. Samples were centrifuged at 14000 rpm for 30 s and cell pellets were resuspended in 50 µl of Laemmli sample buffer (BIO-RAD) containing 5% β-mercaptoethanol.

Samples resuspended in sample buffer were boiled for 5 min and spin down. 5 µl of each sample and 2 µl of Dual Color standard (BIO-RAD) was loaded in to 16.8% SDS-PAGE. Proteins with different sizes were separated in SDS buffer (25 mM Tris, 192 mM glycine, 0.1% SDS) at 200 V for 1 h 10 min. SDS-gels were stained with Coomassie Brilliant Blue R-250 Staining Solution (BIO-RAD) and excess of the dye was removed with 1.7 M acetic acid—2.5 M methanol solution.

To express larger amounts of recombinant protein 50 ml of SOB medium containing 100 µg/ml ampicillin was inoculated with recombinant TOP10 colony. Cells were grown overnight at 37° C. with shaking (225 rpm). In the next morning 1200 ml of fresh SOB medium with 50 µg/ml ampicillin was inoculated with 25 ml of overnight culture. Recombinant cell cultures were grown at 37° C. with shaking until $OD_{600}$ reached 0.6.

To induce the recombinant protein production in the cells IPTG was added to a final concentration of 1 mM. After induction cells were grown for 5 h at 37° C. with shaking. After incubation cultures were centrifuged at 5000 rpm for 17 min and cell pellets were collected and weighted.

Cells were pre washed by suspending them first into $H_2O$ (g/5 ml) and centrifugated at 10000 rpm with SS-34 rotor for 20 min. Second washing step was done with the same ratio of 50 mM Na-phosphate buffer pH 7.0. Centrifugation was repeated and washing was continued with the same ratio of 25 mM Tris, 10 mM EDTA pH 7.3 buffer. In the end of the pre wash cells were centrifuged down once more and weighted.

Example 7

Isolation, Purification and Refolding of Recombinant Reindeer BMP-4 Mature Part with Heparin Binding Site (HBSrdBMP-4)

A. Collection of the *Escherichia coli* TOP10 Cells and Isolation and Purification of Inclusion Bodies Cells were homogenized 1 g (wet weight) cells per 5 ml in cold 0.1 M Tris pH 7, 1 mM EDTA buffer. 1.5 mg Lysozyme (Roche) was added per g of cells in the mixture and cells were incubated 30 min at 4° C. Cells were disrupted with high-pressure homogenizator Cell Disruptor APV-2000. $MgCl_2$ was added to final concentration of 3 mM and DNaseI (Roche) to final concentration of 10 μg/ml and mixture was incubated for 30 min at RT in order to digest DNA.

Half of the mixture volume of 60 mM EDTA, 6% Triton X-100, 1.5 M NaCl pH 7 buffer was added to the solution and mixture was incubated for 30 min at 4° C. Inclusion bodies were spin down by centrifugation at 12000 rpm for 10 min at 4° C. with SS-34 rotor. Pellet was resuspended in ratio of 8 ml per g of cells in 0.1 M Tris pH 7, 20 mM EDTA buffer and centrifugation step was repeated. Inclusion body isolate was weighted and stored in −20° C.

B. IMAC Purification for HBSrdBMP-4

Inclusion body isolate was mixed overnight with stirring to 35 mg/ml to 6 M GuHCl, 0.02 M $Na_2HPO_4$, 0.5 M NaCl pH 8 (lysis buffer). In the next morning solution was centrifuged at 12000 rpm for 20 min with SS-34 rotor. Supernatant was filtered trough Whatman GB 002 paper (Schleicher & Schuell). Centrifugation and filtration was repeated once and sample was stored at 4° C.

Pre-packed HiTrap Chelating HP affinity column (Amersham Biociences) was charged with $Co^{2+}$ ions and equilibrated with sample buffer (lysis buffer pH 8) according to manufactures procedure. 30-40 ml of the filtrated protein sample was applied to the column and washed with 50 ml of lysis buffer pH 8. Second wash was done with 50 ml of 6 M urea, 0.02 M $Na_2HPO_4$, 0.5 M NaCl pH 8.

Desired protein with $His_6$-tag was eluted out of the column with 200 ml of 6 M urea, 0.02 M $Na_2HPO_4$, 0.5 M NaCl pH 4. In final step column was washed with 200 ml of 6 M urea, 0.02 M $Na_2HPO_4$, 0.5 M NaCl, 0.5 M imidazole pH 8. 50 ml fractions were collected during every step. Samples from the fraction were analyzed by SDS-PAGE and fractions containing most recombinant protein were combined.

C. Heparin Affinity Column Purification for Recombinant HBSrdBMP-4

Filtrate obtained after IMAC purification was applied in ready-to-use HiTrap Heparin HP column (Amersham Pharmacia Biotech) which was balanced with 8 M Urea—100 mM Na-phosphate—10 mM Tris-HCl (pH 7.5). The column was then washed with 20 times bed volume of the same buffer and recombinant HBSrdBMP-4 was eluted from the heparin column by NaCl gradient from 0 to 2 M also in the same buffer. The fractions analyzed by SDS-PAGE and Western blot analysis with the highest purity of HBSrdBMP-4 were combined. In Western blot analysis specific antibodies against His6 and BMP-4 were used. Combined fractions were ready for refolding procedure.

D. Refolding of Recombinant HBSrdBMP-4

Refolding of recombinant HBSrdBMP-4 was performed as described in Example 3 part D for recombinant rdBMP-4.

Example 8

The Biological Activity Test of Recombinant Reindeer BMP-4 Mature Part with Heparin Binding Site The biological activity of the lyophilized recombinant reindeer HBSrdBMP-4 was tested by implanting the recombinant protein absorbed into Lyostrypt® collagen sponge or gelatin capsule in mouse tight muscle pouches. BSA was used as control. The hind legs were roentgenographed and the implant sites dissected and fixed in 10% neutral formalin solution. Fixed implants were cut into 7 μm sections and stained with hematoxylin-eosin staining. Sections were examined with a light microscope. The new bone formation as an area and optical density was evaluated by radiographs. The radiographic images were transferred into a computer by using an optical scanner (HP Scan Jet, Hewlett Packard, USA). Ectopic and orthopic new bone formations were evaluated as the areas ($mm^2$) of calcified tissue visible in the radiographs defined by using the Scion Image Beta 4.02 (Scion Corp., USA) software. The mean optical density (mmAl) of the defined area was measured with the same equipment. Calibration of the optical density was performed by using an aluminum wedge (Al) with 0.25 mmAl steps, giving a calibrated density range up to 4 mmAl.

Results

Cloning of partial cDNA of reindeer BMP-4

The nucleotide sequence obtained from ABI Prism reactions was analyzed with computer and it was compared to already known BMP sequences. Due to homology searches the newly cloned cDNA seemed to be most homological with deer BMP-4 (nucleotide homology 99% and amino acid homology 99%) and with mouse, rat, human and dog BMP-4 (amino acid homology 98%). Nucleotide and amino acid homologies of BMP-4 proteins between mammalian species are presented in Table 1.

Expression of Reindeer BMP-4 Mature Part

First, the mature part of reindeer BMP-4 was cloned in pTrcHis2A vector and *E. coli* TOP 10 cells were transformed by resulted pTrcrd4/116 vector. Expression of recombinant protein was induced by IPTG. Recombinant protein production was checked by SDS-PAGE, but no induction was observed. This was expected to be caused by several codons in rdBMP-4 which were rare for *E. coli* codon usage. It could be also possible, that it is caused by high GC content in the beginning of the rdBMP-4 coding sequence (the first 10 codons have a GC content of 70%).

Because of these facts it was decided to try another vector system with different *E. coli* cell lines pET22b(+) (Novagen) with His6-tag and pelB leader was chosen as the new expression vector and Rosetta (DE3) and Origami B (DE3) *E. coli* lines were chosen for expression. The mature part of reindeer BMP-4 was cloned to pET22b(+) and a new plasmid was named as pETrd4 and both Rosetta (DE3) and Origami B (DE3) cells were transformed with the constructed vector. When analyzed by SDS-PAGE, overexpression of rdBMP-4 protein was observed. Due to expression studies mainly Rosetta (DE3) cells with pETrd4 vector were used in producing recombinant rdBMP-4.

Purification of rdBMP-4

Recombinant reindeer rdBMP-4 protein was overexpressed in E. coli. After the wash treatment, isoelectric point precipitation and solubilization of the inclusion bodies the content of recombinant reindeer rdBMP-4 was 85%.

The next purification step was the immobilized metal affinity chromatography (IMAC). After the elution of the column with pH gradient, the purity of rdBMP-4 measured from the SDS-PAGE was up to 75% (FIG. 8). The isolated protein with the mature part of rdBMP-4 had a MW of 17,800 Da as shown by the electrophoretic mobility on SDS-PAGE under reducing conditions.

Refolding and Activity Tests of rdBMP-4

The in vitro refolding of the denatured rdBMP-4 protein was quantified by measuring of the refold dimer of the protein on Coomassie Brilliant Blue stained gels densitometrically. The amount of refolding measured by non-reducing SDS-PAGE was by the protein 50%.

The osteoinductive activity induced by rdBMP-4 was increased in dose dependent manner (Table 2). Table 9 presents in details how the osteoinductive activities were shown on separate animals. The animals were divided in groups, wherein R1-R3 were implanted with different amounts of reindeer BMP-4 and groups R4-R7 with human BMP-4. When compared to its human counterpart the recombinant reindeer BMP-4 was proven to be much more potent inducer of bone formation in all concentrations tested.

Tables 10 and 11 show statistical summaries of comparisons between groups R1-R3 (doses of 5, 3 and 1 mg of rdBMP-4) and between groups R1 (5 mg of rdBMP-4) and R5 (5 mg of human BMP-4), respectively. The analysis of the first group R1-R3 was made with Kruskal-Wallis test and the groups showed statistically significant differences (p=0.023). Groups R1 and R5 were analyzed with Mann-Whitney U-test and also these groups showed statistically significant differences (p=0.032). It is obvious without testing that the differences between the reindeer groups (R1-R3) and the human groups are significant in favor of the reindeer ones. Due to the great number of zero values in the human groups the statistical tests could be applied only between the groups R1 and R5.

TABLE 9

Tested osteoinductive activities of rdBMP-4 and human BMP-4 with different doses.

| Group | Animal number and leg (Left or Right) | Implant Sample (code) | Mass (mg) | Results Area (mm$^2$) |
|---|---|---|---|---|
| R1 | Image 151 - 795 R | rdBMP-4 | 5 | 52 |
| R1 | Image 152 - 796 R | rdBMP-4 | 5 | 2 |
| R1 | Image 152 - 797 R | rdBMP-4 | 5 | 21 |
| R1 | Image 161 - 848 R | rdBMP-4 | 5 | 16 |
| R1 | Image 169 - 898 L | rdBMP-4 | 5 | 0 |
| R1 | Image 172 - 911 L | rdBMP-4 | 5 | 0 |
| R1 | Image 172 - 910 L | rdBMP-4 | 5 | 0 |
| R1 | Image 172 - 909 L | rdBMP-4 | 5 | 0 |
| R1 | Image 180 - 954 R | rdBMP-4 | 5 | 0 |
| R1 | Image 181 - 959 R | rdBMP-4 | 5 | 42 |
| R1 | Image 181 - 958 R | rdBMP-4 | 5 | 44 |
| R1 | Image 181 - 957 R | rdBMP-4 | 5 | 0 |
| R1 | Image 181 - 956 R | rdBMP-4 | 5 | 32 |
| R1 | Image 181 - 955 R | rdBMP-4 | 5 | 32 |
| R1 | Image 181 - 953 R | rdBMP-4 | 5 | 40 |
| R1 | Image 181 - 952 R | rdBMP-4 | 5 | 50 |
| R1 | Image 181 - 951 R | rdBMP-4 | 5 | 47 |
| R1 | Image 181 - 950 R | rdBMP-4 | 5 | 38 |
| R1 | Image 188 - 996 L | rdBMP-4 | 5 | 0 |
| R1 | Image 188 - 998 L | rdBMP-4 | 5 | 0 |
| R2 | Image 151 - 793 R | rdBMP-4 | 3 | 61 |
| R2 | Image 151 - 792 R | rdBMP-4 | 3 | 16 |
| R2 | Image 151 - 790 R | rdBMP-4 | 3 | 21 |
| R2 | Image 161 - 847 R | rdBMP-4 | 3 | 25 |
| R2 | Image 161 - 846 R | rdBMP-4 | 3 | 38 |
| R2 | Image 165 - 872 L | rdBMP-4 | 3 | 23 |
| R2 | Image 164 - 871 L | rdBMP-4 | 3 | 0 |
| R2 | Image 172 - 910 R | rdBMP-4 | 3 | 0 |
| R2 | Image 172 - 908 L | rdBMP-4 | 3 | 0 |
| R2 | Image 178 - 940 R | rdBMP-4 | 3 | 0 |
| R2 | Image 178 - 941 R | rdBMP-4 | 3 | 0 |
| R2 | Image 178 - 942 R | rdBMP-4 | 3 | 0 |
| R2 | Image 178 - 943 R | rdBMP-4 | 3 | 0 |
| R2 | Image 178 - 944 R | rdBMP-4 | 3 | 0 |
| R2 | Image 179 - 945 R | rdBMP-4 | 3 | 17 |
| R2 | Image 179 - 946 R | rdBMP-4 | 3 | 40 |
| R2 | Image 179 - 947 R | rdBMP-4 | 3 | 48 |
| R2 | Image 179 - 948 R | rdBMP-4 | 3 | 39 |
| R2 | Image 179 - 949 R | rdBMP-4 | 3 | 0 |
| R2 | Image 198 - 1037 L | rdBMP-4 | 3 | 28 |
| R3 | Image 151 - 786 R | rdBMP-4 | 1 | 0 |
| R3 | Image 151 - 787 R | rdBMP-4 | 1 | 16 |
| R3 | Image 151 - 788 R | rdBMP-4 | 1 | 22 |
| R3 | Image 151 - 789 R | rdBMP-4 | 1 | 3 |
| R3 | Image 176 - 930 R | rdBMP-4 | 1 | 0 |
| R3 | Image 176 - 931 R | rdBMP-4 | 1 | 0 |
| R3 | Image 176 - 932 R | rdBMP-4 | 1 | 0 |
| R3 | Image 176 - 933 R | rdBMP-4 | 1 | 0 |
| R3 | Image 176 - 934 R | rdBMP-4 | 1 | 0 |
| R3 | Image 177 - 935 R | rdBMP-4 | 1 | 0 |
| R3 | Image 177 - 936 R | rdBMP-4 | 1 | 0 |
| R3 | Image 177 - 937 R | rdBMP-4 | 1 | 0 |
| R3 | Image 177 - 938 R | rdBMP-4 | 1 | 0 |
| R3 | Image 177 - 939 R | rdBMP-4 | 1 | 0 |
| R4 | Image 202 - 1083 R | hBMP-4 | 7.5 | 0 |
| R4 | Image 201 - 1074 R | hBMP-4 | 7.5 | 2 |
| R5 | Image 164 - 867 R | hBMP-4 | 5 | 0 |
| R5 | Image 164 - 868 R | hBMP-4 | 5 | 0 |
| R5 | Image 164 - 869 R | hBMP-4 | 5 | 3 |
| R5 | Image 164 - 870 R | hBMP-4 | 5 | 0 |
| R5 | Image 168 - 887 R | hBMP-4 | 5 | 2 |
| R5 | Image 168 - 886 R | hBMP-4 | 5 | 0 |
| R5 | Image 168 - 886 L | hBMP-4 | 5 | 0 |
| R5 | Image 168 - 885 L | hBMP-4 | 5 | 0 |
| R5 | Image 168 - 887 L | hBMP-4 | 5 | 0 |
| R5 | Image 168 - 885 R | hBMP-4 | 5 | 0 |
| R5 | Image 174 - 925 L | hBMP-4 | 5 | 2 |
| R6 | Image 163 - 863 R | hBMP-4 | 3 | 0 |
| R6 | Image 163 - 864 R | hBMP-4 | 3 | 0 |
| R6 | Image 163 - 865 R | hBMP-4 | 3 | 0 |
| R6 | Image 163 - 866 R | hBMP-4 | 3 | 0 |
| R7 | Image 164 - 867 L | hBMP-4 | 1 | 2 |
| R7 | Image 164 - 866 L | hBMP-4 | 1 | 0 |
| R7 | Image 164 - 868 L | hBMP-4 | 1 | 0 |
| R7 | Image 164 - 865 L | hBMP-4 | 1 | 1 |

TABLE 10

Statistical analysis of different doses of rdBMP-4

| Group | Mean | Standard deviation | n |
|---|---|---|---|
| R1 (5 mg) | 20.8 | 20.8 | 20 |
| R2 (3 mg) | 17.8 | 19.4 | 20 |
| R3 (1 mg) | 2.9 | 7.0 | 14 |

TABLE 11

Statistical analysis of 5 mg doses of rdBMP-4 and hBMP-4

| Group | Mean | Standard deviation | n |
|---|---|---|---|
| R1 (5 mg rdBMP-4) | 20.8 | 20.8 | 20 |
| R5 (5 mg of hBMP-4) | 0.6 | 1.1 | 11 |

Purification of HBSBMP-4 Protein

Recombinant reindeer HBSrdBMP-4 protein was slightly overexpressed in *E. Coli* and produced as inclusion bodies (IBs). After the wash treatment, isoelectric point precipitation and solubilization of the inclusion bodies, they were next purified with the affinity chromatography (IMAC and heparin). After the elution of the columns, the purity of HBSrdBMP-4 measured from the SDS-PAGE was up to 75%. The isolated proteins with the mature part of HBSrdBMP-4 had a MW of 17,700 Da as shown by the electrophoretic mobility on SDS-PAGE under reducing conditions.

Refolding and Activity Tests of HBSrdBMP-4

The in vitro refolding of the denatured HBSrdBMP-4 protein was quantified by measuring of the refold dimer of the protein on Coomassie Brilliant Blue stained gels densitometrically. The amount of refolding measured by non-reducing SDS-PAGE was by HBSBMP-4 protein over 60%.

HBSrdBMP-4 protein produced in *E. coli* TOP10 expression system showed biological activity when implanted in mouse tight muscle pouch. Furthermore, the refolding of the rdBMP-4 with HBS was significantly higher than without HBS, which makes the HBSrdBMP-4 of great value (data now shown).

This invention has been described with an emphasis upon some of the preferred embodiments and applications. However, it will be apparent for those skilled in the art that variations in the disclosed embodiments can be prepared and used and that the invention can be practiced otherwise than as specifically described herein within the scope of the following claims.

---

The invention claimed is:

1. An isolated bone morphogenetic protein 4 (BMP-4) having osteogenic activity, comprising:
   an amino acid sequence that is at least 70% identical to the amino acid sequence of SEQ ID NO: 1, and
   the consensus sequence P-Q-R-A/S-R/K-K/R-K/N/R/L-N/K-K /R/S-N/H/S-C-R/K-R-H-S/A-P.

2. The bone morphogenetic protein 4 of claim 1, comprising the consensus sequence P-Q-R -A/S-R-K-K/R-N/K-K/R-N/H-C-R-R-H-S/A-P.

3. The bone morphogenetic protein 4 of claim 1, comprising the amino acids 6-21 of SEQ ID NO: 1.

4. The bone morphogenetic protein 4 of claim 3, comprising the amino acids 1-23 of SEQ ID NO: 1.

5. The bone morphogenetic protein 4 of claim 4, comprising the amino acid sequence of SEQ ID NO: 1.

6. The bone morphogenetic protein 4 of claim 1, wherein at the amino terminus said protein comprises a heparin binding site comprising the amino acid sequence AKHKQRKRGT (SEQ ID NO: 17).

7. An isolated DNA molecule, encoding the bone morphogenetic protein of claim 1.

8. A nucleotide vector, comprising the isolated DNA molecule of claim 7.

9. A recombinant host cell, comprising the nucleotide vector of claim 8.

10. A pharmaceutical composition, comprising the bone morphogenetic protein of claim 1.

11. The pharmaceutical composition of claim 10, comprising said bone morphogenetic protein as homodimer or as heterodimer together with another bone morphogenetic protein.

12. The pharmaceutical composition of claim 10, further comprising another bone morphogenetic protein, epidermal growth factor, fibroblast growth factor or transforming growth factor.

13. An osteogenic device, comprising the bone morphogenetic protein of claim 1.

14. The osteogenic device of claim 13, comprising said bone morphogenetic protein as homodimer or as heterodimer together with another bone morphogenetic protein.

15. The osteogenic device of claim 13, further comprising another bone morphogenetic protein, epidermal growth factor, fibroblast growth factor or transforming growth factor.

16. The osteogenic device of claim 13, comprising a biocompatible matrix.

17. The osteogenic device of claim 16, wherein said biocompatible matrix comprises calcium phosphate, carboxy methyl cellulose or collagen or combinations thereof.

18. A method for inducing the formation of bone, cartilage, tendon or tooth comprising treating said bone, cartilage, tendon or tooth with the bone morphogenetic protein of claim 1.

19. A method for treating disorders related to bone, cartilage, tendon or tooth wherein regeneration, repair or growth thereof is desired comprising administering the bone morphogenetic protein of claim 1 to a patient suffering from said disorder.

20. The bone morphogenetic protein 4 of claim 2, comprising the amino acids 6-21 of SEQ ID NO: 1.

* * * * *